United States Patent
Jing et al.

(10) Patent No.: US 10,792,383 B2
(45) Date of Patent: Oct. 6, 2020

(54) METHOD OF DISINFECTING A MEDICAL DEVICE

(71) Applicant: 3M INNOVATIVE PROPERTIES COMPANY, Saint Paul, MN (US)

(72) Inventors: Naiyong Jing, Saint Paul, MN (US); Ryan T. Woldt, Minneapolis, MN (US); Wensheng Xia, Woodbury, MN (US); Kevin D. Landgrebe, Woodbury, MN (US); Timothy J. Nies, Stillwater, MN (US); Bryan A. Baker, Minneapolis, MN (US); Semra Colak Atan, St. Louis Park, MN (US); Gary W. Jorgensen, Saint Paul, MN (US); Giuseppe M. Bommarito, Stillwater, MN (US); David P. Swanson, Woodbury, MN (US); George W. Griesgraber, Eagan, MN (US); Ranjani V. Parthasarathy, Saint Paul, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 16/096,776

(22) PCT Filed: Apr. 25, 2017

(86) PCT No.: PCT/US2017/029370
§ 371 (c)(1),
(2) Date: Oct. 26, 2018

(87) PCT Pub. No.: WO2017/192305
PCT Pub. Date: Nov. 9, 2017

(65) Prior Publication Data
US 2019/0105416 A1    Apr. 11, 2019

Related U.S. Application Data

(60) Provisional application No. 62/332,243, filed on May 5, 2016.

(51) Int. Cl.
*A61L 2/00* (2006.01)
*A61L 9/00* (2006.01)
(Continued)

(52) U.S. Cl.
CPC ............... *A61L 2/18* (2013.01); *A01N 33/02* (2013.01); *A01N 35/02* (2013.01); *A61L 2/28* (2013.01); *C12Q 1/22* (2013.01); *A61L 2202/24* (2013.01)

(58) Field of Classification Search
CPC .......... A61L 2/18; A61L 2202/24; A61L 2/28; C12Q 1/22
(Continued)

(56) References Cited

U.S. PATENT DOCUMENTS 4,623,666 A * 11/1986 Kennedy ................ A61K 31/03
514/754
4,980,231 A * 12/1990 Baker .................... A61L 29/041
428/36.9
(Continued)

FOREIGN PATENT DOCUMENTS

EP    1707943    10/2006
EP    1756295    2/2007
(Continued)

OTHER PUBLICATIONS

Feng, "A Simple and Highly Sensitive Colorimetric Detection Method for Gaseous Formaldehyde", J. Am. Chem. Soc. 2010, 132, 4046-4047.
(Continued)

*Primary Examiner* — Monzer R Chorbaji
(74) *Attorney, Agent, or Firm* — 3M Innovative Properties Company; Trisha D. Adamson

(57) ABSTRACT

A method of disinfecting a medical device comprises three steps. First, a disinfectant is contacted with a process indi-
(Continued)

cator and the medical device. The disinfectant comprises at least one aldehyde. The process indicator contains a synthetic amine-containing compound disposed on a substrate. The synthetic amine-containing compound comprises at least one of primary amino groups or secondary amino groups, and is reactive with the disinfectant to form at least one adduct. The synthetic amine-containing compound and the medical device are in fluid communication through the disinfectant. A predetermined disinfectant exposure criterion exists for contacting the disinfectant with the medical device. Second, the process indicator is spectrally observed and at least one parameter is obtained therefrom that is predictive of the predetermined disinfectant exposure criterion. The third step is determining that the predetermined disinfectant exposure criterion has been achieved.

21 Claims, 1 Drawing Sheet

(51) Int. Cl.

| | | |
|---|---|---|
| *B08B 7/00* | (2006.01) | |
| *B08B 9/04* | (2006.01) | |
| *A61L 2/18* | (2006.01) | |
| *A61L 2/28* | (2006.01) | |
| *A01N 35/02* | (2006.01) | |
| *A01N 33/02* | (2006.01) | |
| *C12Q 1/22* | (2006.01) | |

(58) Field of Classification Search
USPC .................. 422/28, 32, 36; 134/6, 8, 22.1
See application file for complete search history.

(56) References Cited

U.S. PATENT DOCUMENTS

| | | | |
|---|---|---|---|
| 5,352,368 A | 10/1994 | Honeycutt | |
| 6,068,815 A * | 5/2000 | Oberleitner | A01N 37/16 |
| | | | 134/170 |
| 6,436,716 B1 * | 8/2002 | Wu | G01N 31/22 |
| | | | 422/423 |
| 6,793,880 B2 | 9/2004 | Kippenhan, Jr. | |
| 6,897,059 B2 | 5/2005 | Foltz | |
| 7,247,482 B2 | 7/2007 | Lemus | |
| 7,468,272 B2 | 12/2008 | Chandrapati | |
| 7,524,673 B2 | 4/2009 | Gonzalez | |
| 8,343,768 B2 | 1/2013 | Kyung-Hee Song | |
| 8,357,083 B2 | 1/2013 | Nagai | |
| 8,551,894 B2 | 10/2013 | Seshadri | |
| 8,597,959 B2 | 12/2013 | Jing | |
| 2007/0154703 A1 | 7/2007 | Waller | |
| 2009/0081767 A1 | 3/2009 | Ogawa | |
| 2012/0009396 A1 | 1/2012 | Sikka | |
| 2012/0252091 A1 | 10/2012 | Rasmussen | |
| 2013/0302630 A1 * | 11/2013 | Ono | C09D 5/02 |
| | | | 428/523 |
| 2014/0369953 A1 * | 12/2014 | Purschwitz | A01N 37/04 |
| | | | 424/78.36 |
| 2015/0203790 A1 | 7/2015 | Strerath | |
| 2015/0232673 A1 | 8/2015 | Jing | |
| 2015/0246350 A1 | 9/2015 | Sun | |
| 2015/0252196 A1 | 9/2015 | Jing | |
| 2016/0096802 A1 | 4/2016 | Rasmussen | |

FOREIGN PATENT DOCUMENTS

| | | | |
|---|---|---|---|
| EP | 1756295 B1 | 8/2011 | |
| WO | WO 03/028772 | 4/2003 | |
| WO | WO 2009-137442 | 11/2009 | |
| WO | WO 2014-008150 | 1/2014 | |
| WO | WO 2014/209798 | 12/2014 | |
| WO | WO 2016-149472 | 9/2016 | |
| WO | WO 2016-149571 | 9/2016 | |
| WO | WO 2016-164329 | 10/2016 | |
| WO | WO 2017-184444 | 10/2017 | |
| WO | WO 2017-184664 | 10/2017 | |
| WO | WO 2017-192306 | 11/2017 | |

OTHER PUBLICATIONS

Medivators Inc., "Rapicide OPA/28 Test Strips Quality Control Procedure", 2014, 2 pages.
Metrex, "Quick Reference for Using Metritest Test Strips", (date unknown but believed to be prior to the date of the filing of the present application) 1 page.
Product Label, "Rapicide Glutaraldehyde Indicator Test Strips", A Product from Medivators Inc., (date unknown but believed to be prior to the date of the filing of the present application) 1 page.
Product Label, "Rapicide OPA/28 Test Strip", A Product from Medivators Inc., (date unknown but believed to be prior to the date of the filing of the present application),1 page.
Product Literature, "3M™ Comply™ Cold SteriLog™ Glutaraldehyde Monitors 3983MM, 3987, 3989", A Product of 3M Health Care, 2015, 2 pages.
Product Literature, "Cidex OPA Solution Test Strips", A product of Advanced Sterilization Products, A Division of J&J Medical Ltd., 2004, 6 pages.
Product Literature, "Cidex OPA Solution", A product of Advanced Sterilization Products, A Division of J&J Medical Ltd., 2011, 2 pages.
Product Literature, "Disintek GTA 1.5%Test Strips", A Product of Serim Research Corporation, (date unknown but believed to be prior to the date of the filing of the present application) 2 pages.
Product Literature, "Disintek GTA 2.1%Test Strips", A Product of Serim Research Corporation, (date unknown but believed to be prior to the date of the filing of the present application) 2 pages.
Product Literature, "Disintek OPA Test Strips", A Product of Serim Research Corporation, 2013, 2 pages.
Product Literature, "Opal: Instrument Grade—High Level Disinfectant", Whiteley Medicals, (date unknown but believed to be prior to the date of the filing of the present application) 2 pages.
Product Literature, "Quantofix Glutaraldehyde", A Product of Macherey-Nagel GMbH and CO, 2009, 1 page.
Product Literature, "Rapicide Glutaraldehyde Indicator Test Strips", A Product from Medivators Inc., 2011, 2 pages.
Product Literature, "Rapicide OPA/28 Test Strips", A Product from Medivators Inc., 2014, 2 pages.
Product Profile, "Disintek GTA 1.5% Test Strips", A Product of Serim Research Corporation, 2010, 1 page.
Product Profile, "Disintek OPA Test Strips", A Product of Serim Research Corporation, 2015, 1 page.
Quick Reference Guide "Medivators Rapicide Test Strips", A Product from Medivators Inc., 2015, 1 page.
SGNA, "Standards of Infection Prevention in Reprocessing of Flexible Gastrointestinal Endoscopes", Society of Gastroenterology Nurses and Associates, Inc. 2015, 31 pages.
Wang, "Nanofibrous Polyethyleneimine Membranes as Sensitive Coatings for Quartz Crystal Microbalance-Based Formaldehyde Sensors", Sensors and Actuators B: Chemical, 2010, vol. 144, pp. 11-17.
PCT International Search Report for PCT/US2017/029370 dated Sep. 20, 2017.

* cited by examiner

METHOD OF DISINFECTING A MEDICAL DEVICE

CROSS REFERENCE TO RELATED APPLICATIONS

This application is a national stage filing under 35 U.S.C. 371 of PCT/US2017/029370, filed Apr. 25, 2017, which claims the benefit of U.S. Provisional Pat. Application No. 62/332,243, filed May 5, 2016, the disclosures of which are incorporated by reference in their entirety herein.

TECHNICAL FIELD

The present disclosure relates to methods of disinfecting medical devices using liquid disinfectant.

BACKGROUND

Reusable medical devices or items that touch mucous membranes are commonly used in the medical arts. Examples of such devices include reusable flexible endoscopes, endotracheal tubes, anesthesia breathing circuits, and respiratory therapy equipment. When inserted into the body, these medical devices may become heavily contaminated with patient biomaterial and microorganisms, including potential pathogens. Careful reprocessing of the medical devices is critical to reducing the risk of cross-contamination and the possible transmission of pathogens between patients.

Flexible endoscopes are rated as semi-critical according to the Spaulding classification for medical devices, and therefore it is required that these devices be decontaminated by high level disinfection. Thus, it is recommended that both endoscopes and reusable accessories be frequently visually inspected in the course of their use and reprocessing, including before, during and after use, as well as after cleaning and before high-level disinfection. However, a visually based method of verification has severe limitations when applied to flexible endoscopes because the complex, narrow lumens in these devices cannot be directly visually inspected.

Automated endoscope reprocessors (AERs) are used to clean and disinfect flexible endoscopes to a level that mitigates transmission of pathogenic organisms and disease between patients who are subject to an endoscopic procedure. To disinfect AERs, a liquid disinfectant is typically recirculated through the AER for a prescribed time. Typically, the only information available to a user is the parametric information provided by the AER equipment itself which consists primarily of time and temperature information. The AER does not monitor chemically-related parameters capable of establishing the efficacy of the disinfection cycle.

SUMMARY

In one aspect, the present disclosure provides a method of disinfecting a medical device, the method comprising steps:

a) contacting a disinfectant with a process indicator and the medical device, wherein the disinfectant comprises at least one aldehyde, wherein the process indicator contains a synthetic amine-containing compound disposed on a substrate, wherein the synthetic amine-containing compound is reactive with the disinfectant to form at least one adduct, wherein the synthetic amine-containing compound and the medical device are in fluid communication through the disinfectant, wherein a predetermined disinfectant exposure criterion exists for contacting the disinfectant with the medical device, and wherein the synthetic amine-containing compound comprises at least one of primary amino groups or secondary amino groups; and b) spectrally observing the process indicator and obtaining at least one parameter therefrom that is predictive of the predetermined disinfectant exposure criterion; and c) determining that the predetermined disinfectant exposure criterion has been achieved.

In some embodiments, the synthetic amine-containing polymer comprises at least one of:
i) branched polyethylenimine (PEI);
ii) branched PEI that has been e-beam grafted to the substrate;
iii) crosslinked branched PEI;
iv) crosslinked branched guanylated polyethylenimine; or
v) crosslinked branched silylated polyethylenimine.

In some embodiments, the synthetic amine-containing polymer comprises an amine-functional polysiloxane.

In some embodiments, the synthetic amine-containing compound comprises a polyethylenimine that is chemically bonded to silica.

Advantageously, the present disclosure provides suitable methods and materials for confirming that a predetermined disinfectant exposure criterion was achieved during the disinfection process.

As used herein, the term "amine-functional" means containing at least one amino group.

As used herein, the term "synthetic" refers to something man-made (i.e., not naturally occurring).

As used herein, the term "optical reflectance" means reflectance of at least one wavelength in the range of from 350 to 750 nanometers (nm).

As used herein, the term "visible color" means color visible in the wavelength range of from 400 to 700 nm.

As used herein, the term "inert" means not chemically reactive under environmentally ambient conditions with other organic components of the composition in which it is a component.

As used herein, the term "spectrally" means involving one or more wavelengths of electromagnetic radiation.

Features and advantages of the present disclosure will be further understood upon consideration of the detailed description as well as the appended claims.

Figure 1:
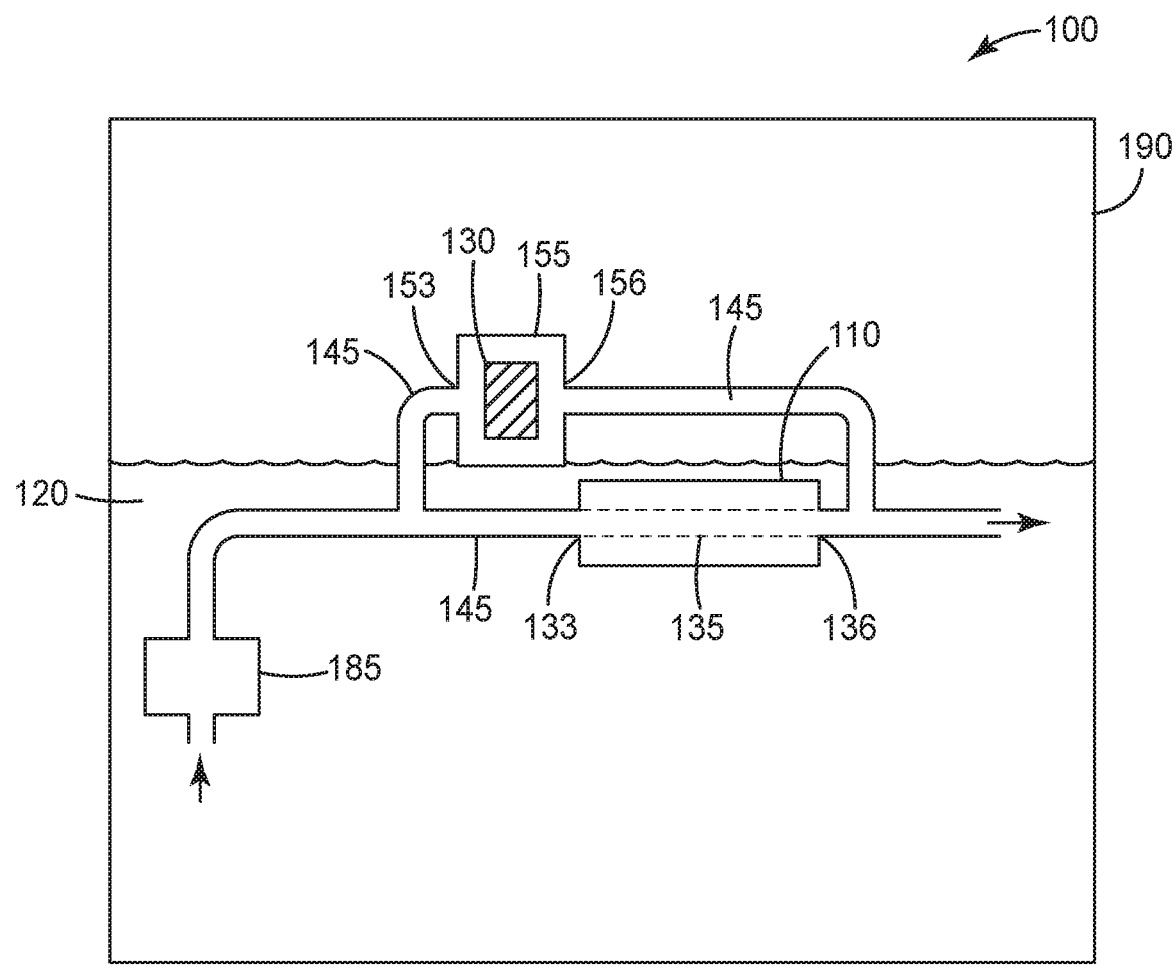
FIG. 1 is a schematic process flow diagram illustrating an exemplary method 100 of disinfecting a medical device according to the present disclosure.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

Referring now to FIG. 1, a method 100 of disinfecting an endoscope 110 includes at least three steps a), b), and c), which may be carried out in conjunction with automatic reprocessor 190.

Step a) includes contacting a disinfectant 120 with a process indicator 130 and the medical device 110. Disinfectant 120 is recirculated through endoscope 110 and process indicator module 155 by pump 185. Disinfectant 120 is diverted through tubing 145 such that process indicator module 155 is in parallel flow with endoscope 110. Endoscope 110 has a first inlet port 133, and a first outlet port 136 and internal conduit 135 extending therebetween. Process indicator module 155 has second inlet port 153 and second outlet port 156. While shown in a parallel configuration, it is also contemplated that an "in line" or "in bath" configuration may also be used.

Figure 2:
FIG. 2 is an enlarged schematic side view of process indicator 130 in FIG. 1.

Disinfectant 120 comprises at least one aldehyde. Process indicator 130 contains a synthetic amine-containing compound 140 disposed on a substrate 150 (see FIG. 2). Synthetic amine-containing compound 140 comprises at least one of primary amino groups or secondary amino groups. Synthetic amine-containing compound 140 is reactive with disinfectant 120 to form at least one adduct. Synthetic amine-containing compound 140 and the medical device 110 are in fluid communication through disinfectant 120. A predetermined disinfectant exposure criterion exists for contacting disinfectant 120 with medical device 110.

Step b) includes spectrally observing (e.g., by reflectance, transmission, and/or fluorescence spectroscopy) the process indicator 130 and obtaining at least one parameter (e.g., reflectance, transmission, and/or fluorescence at one or more wavelengths) therefrom that is predictive of the predetermined disinfectant exposure criterion. For example, observation may be made at one or more wavelengths, which may optionally be compared to a reference wavelength.

Step c) includes determining that the predetermined disinfectant exposure criterion has been achieved. This step typically involves comparing the observed parameter to a value of the parameter corresponding to the predetermined disinfectant exposure criterion, and then determining that the predetermined disinfectant exposure criterion has been achieved. If not, the process is continued until the predetermined disinfectant exposure criterion is met, or the entire cycle is repeated.

Examples of suitable medical devices for practicing the present disclosure include, for example, a grasper (e.g., forceps), a clamp, an occluder, a retractors, a distractor, a positioner, a stereotactic device, a mechanical cutter (e.g., a scalpel, a lancet, a rasp, a trocar, a drill bit, a rongeur, a reamer, a ridged reamer, a bone curette, a scissors, a broach), a dilator, a speculum, a sealing device (e.g., a surgical stapler), a needle (e.g., for irrigation or injection), a tip (e.g., for irrigation or suction), a tube (e.g., for irrigation or suction), a tool (e.g., a hip impactor, a screwdriver, a spreader, a hammer, a spreader brace, a probe, a carrier, an applier, a cutting laser guide, a ruler, a calipers, a drill key), a powered device (e.g., a dermatome, an ultrasonic tissue disruptor, a cryotome, a drill), and a lumened device. Lumened devices have at least one internal conduit through which the disinfectant may be introduced. Examples of lumened devices include endoscopes such as, for example, an arthroscope, a laparoscope, a thoracoscope, a cystoscope, a rhinoscope, a bronchoscope, a colonscope, a choledochoscope, an echoendoscope, an enteroscope, an esophagoscope, a gastroscope, a laryngoscope, a rhinolaryngoscope, a sigmoidoscope, and a duodenoscope.

In embodiments wherein the medical device comprises an endoscope, a user would first connect a process indicator module containing the process indicator directly to the AER machine using a harness modified from that used to connect the endoscope to allow connection of the internal conduit(s) of the endoscope in a parallel fashion (although serial connection is also contemplated). The process indicator module has a fluid intake comprising an inlet port and a fluid output comprising an outlet port for circulating the disinfectant through the process indicator module. The intake for the process indicator module would be placed in a basin of the AER that also holds the endoscope to be reprocessed. The process indicator module may be apart from, or fully or partially immersed in the disinfectant as long as the intake and optionally the output are in fluid communication with the disinfectant.

The process indicator module comprises, and typically contains, the process indicator such that the process indicator is in contact with the disinfectant liquid during the disinfection cycle. The process indicator module may have any form that performs the intended function. In some embodiments, the process indicator module may have a tortuous fluid path that mimics a tortuous path through the medical device (e.g., endoscope). Typically, the process indicator is disposed on a substrate within the process indicator module, however it may be self-supporting in some embodiments. An example of a suitable AER and process indicator module can be found in PCT Pat. Appl. No. US2016/025970, filed Apr. 5, 2016, and entitled "Process Challenge Device for Automated Endoscope Reprocessor". Additional suitable related apparatuses can be found in U.S. Provisional Pat. Appln. Nos. 62/326329, entitled "Removable Cartridges for Use with Process Monitoring Systems, and Systems Comprising Same", filed Apr. 22, 2016, and 62/326323, entitled "Readers for Process Monitoring Systems and Methods of Use", filed Apr. 22, 2016.

After completion of a disinfecting cycle, the user may observe (e.g., visually or instrumentally) the process indicator to determine whether the predetermined disinfectant exposure (e.g., minimum effective concentration (MEC), time, and/or temperature) was achieved. If not, the process may be continued or restarted, for example. Examples of instrumental methods for observing the process indicator include observation by human eye, reflectance spectroscopy, transmission spectroscopy, fluorescence spectroscopy, phosphorescence spectroscopy, and electrical capacitance. Such methods are well known in the art, and may use corresponding commercially available equipment.

If observation of the process indicator indicates inadequate disinfection relative to a predetermined disinfectant exposure criterion (i.e., FAIL), further processing would ordinarily be carried out until the process indicator indicates adequate disinfection relative to the predetermined disinfectant exposure criterion (i.e., PASS), or the medical device can be optionally re-cleaned and the entire process repeated. If observation of the process indicator indicates adequate disinfection relative to the predetermined disinfectant exposure criterion (i.e., PASS), then the disinfection/cleaning process can be discontinued.

The disinfectant may comprise an aldehyde known for disinfecting medical equipment such as, for example, formaldehyde and dialdehydes (e.g., glutaraldehyde or orthophthalaldehyde), and combinations thereof The disinfectant may include the aldehyde(s) in a liquid vehicle such as, for example, water, organic solvent (e.g., propylene glycol), or a mixture thereof. Appropriate dilution levels may be dictated by industry and/or regulatory standards.

Typically, the process indicator is disposed (e.g., as a thin film or coating) on a substrate, although this is not requirement. Methods applying films and coatings to a substrate are well known in the art, and include, for example, dip coating, spraying, roll coating, gravure coating, slot coating, spin coating, or brush coating. Preferably, the substrate is selected to be unreactive with the disinfectant. The substrate may be porous or impermeable, and/or opaque or transparent, for example. Examples of suitable substrates include paper, metal, glass, and/or plastic (e.g., polyethylene, polypropylene, polyethylene terephthalate, acrylics, polycarbonates, polyamides, polyurethanes, silicones, and polystyrene) sheets, films, membranes, and fabrics (e.g., nonwoven, or woven). In general, the thickness of the thin film or coating is not particularly important; however, it is preferable that a sufficient amount of the synthetic amine-containing compound is present such that facile and accurate observation of the reacted (i.e., with the disinfectant) synthetic amine-containing compound can be performed.

When the concentration of the aldehyde in the disinfectant is sufficient, reaction of the aldehyde with the synthetic amine-containing compound results in products that may have a color and/or other spectral property (e.g., dielectric constant) change that can be readily observed.

Primary amines can react with aldehydes to form imines, or in the case of some dialdehydes, phthalimidines and/or dimeric products as shown in Scheme I, below:

SCHEME I

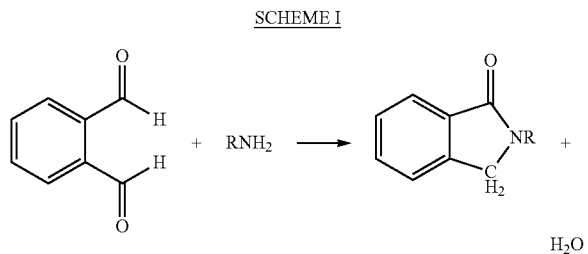

wherein R represents a hydrocarbyl group (e.g., aralkyl, alkaryl, aryl, alkyl). In some cases, a resulting imine may tautomerize to form a corresponding enamine (e.g., see below). In the case of formaldehyde, reaction with a primary amine typically results in methylation of the primary amine nitrogen.

Lacking two amino hydrogens, secondary amines may react with some aldehydes (e.g., aliphatic aldehydes) to form enamines, for example, as shown for the particular example in Scheme II, below:

SCHEME II

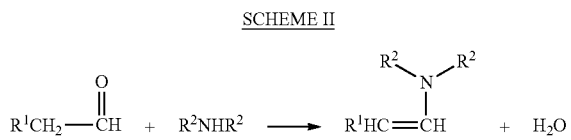

wherein $R^1$ represents a monovalent organic group, and each $R^2$ independently represents a hydrocarbyl group. Depending on the type of aldehyde, other types of reaction products may be observed. In both cases, the reaction products may exhibit visible color or fluorescence, for example.

Typically, the amount of reaction product(s) formed is a function of both the concentration of the amine and the aldehyde, and the time they are in contact. Such a process indicator functions as configured as a time-concentration-temperature integrator, meaning that it will measure the total exposure of the amine to the aldehyde. This can be done by using a relatively non-reactive synthetic polyamine compound, or in the case of highly reactive synthetic polyamine compounds by providing a process indicator that includes a wicking strip, and allowing for capillary action in the wicking material to dictate the flow of disinfectant along the strip; visualization of the colorimetric front along the strip would then become an indication of time, as well as MEC. The porosity of the strip can be chosen to achieve a desired movement of disinfectant along the strip for a given cycle duration. The wicking strip may be made of an appropriate membrane or filtration material, for example.

The predetermined disinfectant exposure criterion may correspond to an industry and/or governmental standard and/or guidelines or protocol for disinfection of the medical device, or the medical device manufacturer's specific disinfection procedure. Examples include ANSI/AAMI ST91: 2015 "Flexible and semi-rigid endoscopic processing in health care facilities", American National Standards Institute, Washington, D.C., and "Standards of Infection Prevention in Reprocessing of Flexible Gastrointestinal Endoscopes", Society of Gastroenterology Nurses and Associates, Inc. (SGNA), Chicago, Ill., 2015.

The parameter to be monitored may be any parameter that correlates directly or indirectly with the amount of reaction product of the aldehyde(s) in the disinfectant with the process indicator that is formed. Exemplary parameters may include visible color (or color change), reflectance at one of more wavelengths, capacitance, and fluorescence at one or more wavelengths. The parameter(s) may be obtained continuously or periodically.

The process indicator relies at least in part on the reaction of aldehyde in the disinfectant with one or more synthetic amine-containing compounds. In some exemplary embodiments, the synthetic amine-containing compound comprises at least one synthetic amine-containing polymer. In some preferred embodiments, the synthetic amine-containing polymer is derived from PEI.

PEI is available in several forms such as linear, branched, and dendrimeric. Linear PEI can be represented by Formula I, below:

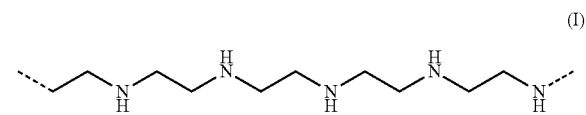

(I)

wherein - - - indicates continued linear polymeric ethylenimine-derived units or H. Linear PEI is available by post-modification of other polymers like poly(2-oxazolines) or N-substituted aziridines. Linear PEIs are commercially available and/or can be made according to known methods.

An exemplary branched PEI fragment can be represented by Formula II, below:

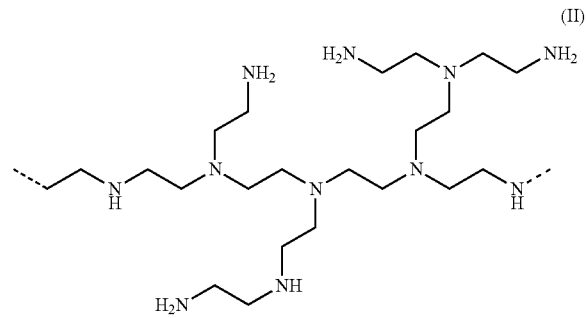

(II)

wherein - - - indicates continued linear and/or branched polymeric ethylenimine-derived units or H. As branching is typically more or less random, branched PEIs typically contain many compounds of this general type as a mixture. Branched PEI can be synthesized by the ring opening polymerization of aziridine. Branched PEIs are commercially available and/or can be made according to known methods.

Dendrimeric PEI is a special case of a branched PEI. An exemplary (generation 4) dendrimeric PEI is represented by Formula III, below:

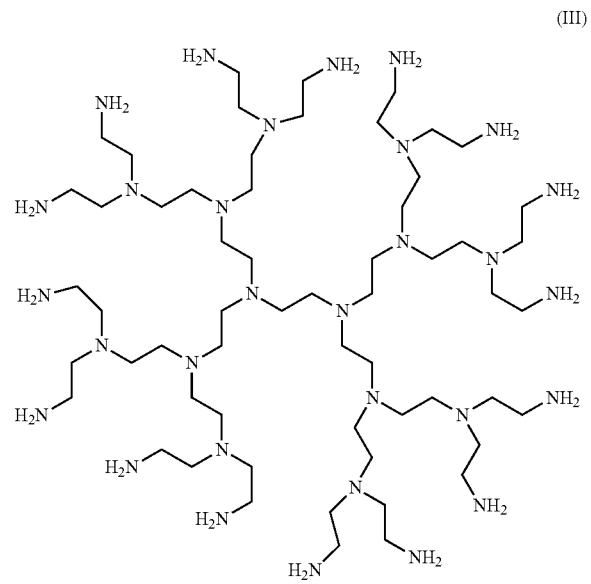 [SMILES: NCCN(CCN)CCN(CCN(CCN)CCN)CCN(CCN(CCN(CCN)CCN)CCN(CCN)CCN)CCN(CCN(CCN(CCN)CCN)CCN(CCN)CCN)CCN(CCN(CCN)CCN)CCN(CCN)CCN]

(III)

In this case, the PEI contains only primary and tertiary amino groups. Dendrimeric PEIs are commercially available and/or can be made according to known methods.

For the purposes of this application, the term "polyethylenimine" also includes ethoxylated polyethylenimine, which can be formed by reaction of some or all (preferably less than 50 percent, less than 30 percent, or even less than 10 percent) of the primary amino groups with one or more molecules of ethylene oxide. As used herein, the term "polyethylenimine" also includes protonated forms.

In one embodiment, the process indicator comprises, consists essentially of, or even consists of, at least one branched PEI. While such embodiments can be effective as indicators, there may be a tendency of the branched PEI to leach into the disinfectant. For this reason, it may be desirable to reduce the leaching rate of the PEI. This embodiment may be useful, for example, if glutaraldehyde is used in the disinfectant, since glutaraldehyde, which is a dialdehyde, may effect crosslinking of the branched PEI when it reacts with the primary amino groups.

In another embodiment, leaching is reduced or eliminated by e-beam grafting the branched PEI to a substrate on which it is disposed. In one method, the substrate is contacted with PEI and exposed to e-beam radiation sufficient to cause grafting. Electron beam generators are commercially available from a variety of sources, including the ESI "ELECTROCURE" EB SYSTEM from Energy Sciences, Inc. (Wilmington, Mass.), and the BROADBEAM EB PROCESSOR from PCT Engineered Systems, LLC (Davenport, Iowa). For any given piece of equipment and irradiation sample location, the dosage delivered can be measured in accordance with ASTM E-1275 entitled "Practice for Use of a Radiochromic Film Dosimetry System". By altering extractor grid voltage, beam diameter and/or distance to the source, various dose rates can be obtained. Exemplary e-beam doses may be from about 5 kilograys (kGys) to about 100 kGys, at an accelerating voltage of 150 to 400 keV, preferably 250 to 350 keV. E-beam grafting can also be accomplished by methods such as, for example, those described in U.S. Pat. No. 8,551,894 (Seshadri et al.), wherein an amine-reactive ligand (e.g, a bromine atom or an acryloxy group) is grafted onto the substrate, and then the resulting functionalized substrate is contacted with PEI resulting in a chemical reaction that bonds the PEI to the substrate. Further details concerning e-beam grafting of PEI to a substrate can be found in U.S. Pat. Appl. Publ. No. 2007/0154703 (Waller et al.). Suitable substrates are preferably porous, although this is not a requirement.

Leaching can be reduced also by washing the PEI-coated substrate during manufacture so that the PEI-coated substrate does not contain extraneous PEI that can leach into the AER disinfectant or rinse solutions.

The molecular weight of the PEI may be tailored depending on specific application requirements. In some embodiments, the PEI has a molecular weight ($M_w$) of 500 to 1500 g/mole. In some embodiments, the PEI has a molecular weight ($M_w$) of 1500 to 2000 g/mole. In some embodiments the PEI has a molecular weight ($M_w$) of 2000 to 5000 g/mole. In some embodiments the PEI has a molecular weight ($M_w$) of 5000 to 15000 g/mole. In some embodiments the PEI has a molecular weight ($M_w$) of 15000 to 30000 g/mole. In some embodiments the PEI has a molecular weight ($M_w$) of 30000 to 60000 g/mole. In some embodiments the PEI has a molecular weight ($M_w$) of 60000 to 100000 g/mole. In some embodiments the PEI has a molecular weight ($M_w$) of greater than or equal to 100000 g/mole.

Exemplary substrates for e-beam grafting include porous membranes, porous nonwoven webs, papers, and porous fibers. The porous base substrate may be formed from any suitable polymeric material. Suitable polymeric materials include, but are not limited to, polyolefins, poly(isoprenes), poly(butadienes), fluorinated polymers, chlorinated polymers, polyesters, polyamides, polyimides, polyethers, poly (ether sulfones), poly(sulfones), polyphenylene oxides, poly (vinyl acetates), copolymers of vinyl acetate, poly (phosphazenes), poly(vinyl esters), poly(vinyl ethers), poly (vinyl alcohols), and poly(carbonates). Suitable polyolefins include, but are not limited to, poly(ethylene), poly(propylene), poly(1-butene), copolymers of ethylene and propylene, alpha olefin copolymers (such as copolymers of 1-butene, 1-hexene, 1-octene, and 1-decene), poly(ethylene-co-1-butene) and poly(ethylene-co-1-butene-co-1-hexene). Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene). Suitable polyamides include, but are not limited to, poly (imino(1-oxohexamethylene)), poly(iminoadipoyliminohexamethylene), poly(iminoadipoyliminodecamethylene), and polycaprolactam. Suitable polyimides include, but are not limited to, poly(pyromellitimide). Suitable poly(ether sulfones) include, but are not limited to, poly(diphenylether sulfone) and poly(diphenylsulfone-co-diphenylene oxide sulfone). Suitable copolymers of vinyl acetate include, but are not limited to, poly(ethylene-co-vinyl acetate) and such copolymers in which at least some of the acetate groups have been hydrolyzed to afford various poly(vinyl alcohols). In some embodiments, cellulosic paper may be used, alone, or in combination with film or membranes of the foregoing polymeric materials.

In some embodiments, the polyethylenimine is cross-linked prior to, or simultaneous with, by reaction with the amine-reactive hydrolyzable organosilane using a chemical crosslinker. Suitable crosslinkers have a plurality (e.g., 2, 3, 4, or 5) of amine-reactive groups that form covalent bonds to the amino groups. Preferably, the crosslinker has two amine reactive groups. Typically, crosslinking is effected by simply combining the PEI and the crosslinker under relatively high dilution conditions (favoring intramolecular crosslinking) to minimize gelation caused by interchain crosslinking. Determination of appropriate conditions is within the capabilities of those skilled in the art.

Examples of suitable crosslinkers may include crosslinkers represented by the formula

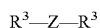

$R^3$ represents an amine-reactive group containing 1 to 12 carbon atoms. Preferably, $R^3$ contains 1 to 8 carbon atoms, more preferably 1 to 6 carbon atoms, and even more preferably 1 to 3 carbon atoms. Exemplary amine-reactive groups $R^3$ include an isocyanato group (—N=C=O), an oxiranyl group

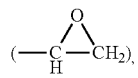

a glycidoxy group

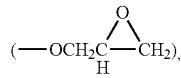

an acryl group

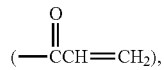

an acryloxy group

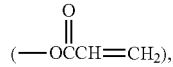

carboalkoxy groups having from 2 to 5 carbon atoms (e.g., carboethoxy group

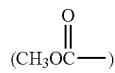

or a carbomethoxy group

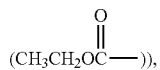

a vinylsulfonyl group

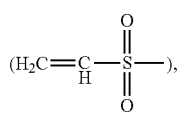

cyclic anhydride groups

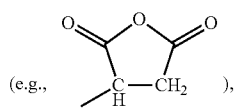

alkylcarbamato groups

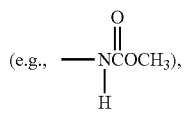

haloalkyl groups (e.g., $BrCH_2$— or $ClCH_2$—), and acrylamido groups

Z represents a divalent organic group (e.g., alkylene having from 1 to 8 carbon atoms (e.g., methylene, ethylene, propylene, butylene, pentylene, hexylene)), which may be linear, branched, or cyclic.

Suitable crosslinkers for PEIs include, for example, polyfunctional compounds such as: halohydrins (e.g., epichlorohydrin); polyfunctional acrylates (e.g., 1,6-hexanediol diacrylate, ethylene glycol diacrylate, diethylene glycol diacrylate, triethylene glycol diacrylate, tetraethylene glycol diacrylate, ethoxylated trimethylolpropane triacrylates, trimethylolpropane triacrylate, glycerol triacrylate, dipentaerythritol hexaacrylate); dialdehydes (e.g., alkyl, aryl or alkaryl dialdehydes such as oxaldehyde, malondialdehyde, propanedialdehyde, succinaldehyde, glutaraldehyde, adipaldehyde, 2-hydroxy-hexanedial, phthalaldehyde, 1,4-benzenediacetaldehyde, 4,4-(ethylenedioxy)dibenzaldehyde, and 2,6-naphthalenedialdehyde); diepoxides (e.g., aliphatic, cycloaliphatic and glycidyl ether diepoxides such as, for example, vinylcyclohexene dioxide, 3,4-epoxycyclohexylmethyl 3,4-epoxycyclohexanecarboxylate, 3,4-epoxy-6-methylcyclohexylmethyl 3,4-epoxy-6-methylcyclohexanecarboxylate, bis(3,4-epoxy-6-methylcyclohexylmethyl) adipate, dipentene dioxide, diglycidyl ether of bis-phenol A, diglycidyl ether of bis-phenol F, 1,4-butanediol diglycidyl ether); diesters (e.g., diethyl adipate, dimethyl fumarate, diethyl sebacate, and dimethyl maleate); divinylsulfone; polyfunctional acrylamides (e.g., piperazine diacrylamide, diacrylamide, N,N-methylene diacrylamide, and N,N'-(ethane-1,2-diyl) diacrylamide); polyisocyanates (e.g., hexamethylene diisocyanate, methylene diisocyanate), and polyaziridinyl compounds (e.g., tris-(1-aziridinyl)phosphine oxide), carbodiimides (e.g., 1-ethyl-3-(3-dimethylaminopropyl) carbodiimide), and N-hydroxysuccinimide. Additional crosslinkers are known in the art, and will be available to those of skill in the art.

Preferably, an amount of the crosslinker is used that results in reaction with from 1 to 10 percent of the available primary nitrogen atoms in the PEI, more preferably 3 to 8 percent.

In some embodiments, an increase in the ratio of secondary to primary amines results in higher contrast in color or other spectral measurement. For example, the ratio of secondary to primary amines in the PEI may be at least 1:1, at least 3:1, at least 5:1, or even at least 10:1.

The crosslinker is used in considerably less than equivalent quantity (or stoichiometric ratio) with respect to the primary and/or secondary amino groups to leave at least one fourth, and preferably one-half or somewhat more of the NH groups in the polymer unreacted. If desired, an excess of unreacted PEI may be added to the solution of partially crosslinked polymeric reaction product to increase the overall average frequency of unreacted NH groups.

In another embodiment, the process indicator comprises, consists essentially of, or consists of at least one crosslinked branched guanylated PEI. Guanylated PEIs can be made using a guanylating agent, for example, according to the procedures described in U.S. Pat. Appl. Publ. No. 2016/0096802 (Rasmussen et al.). As used herein, the term "guanylating agent" means a compound that is reactive with an amino moiety of an amine compound to provide a guanidino-functional compound (e.g., reaction of the guanylating agent with the amino moiety can form a guanidino moiety in situ through an addition reaction or a displacement reaction).

Exemplary guanylating agents include O-alkylisourea salts, S-alkylisothiourea salts, carbodiimides, cyanamides, amidino-functional salts, and combinations thereof. Preferred guanylating agents include O-alkylisourea salts, carbodiimides, and combinations thereof Representative examples of suitable guanylating agents that can react with amines through displacement reactions include O-methylisourea sulfate (also known as O-methylisourea hemisulfate), O-methylisourea hydrogen sulfate, O-methylisourea acetate, O-ethylisourea hydrogen sulfate, O-ethylisourea hydrogen chloride, S-methylisothiourea sulfate (also known as S-methylisothiourea hemisulfate), S-methylisothiourea hydrogen sulfate, S-methylisothiourea acetate, S-ethylisothiourea hydrogen sulfate, S-ethylisothiourea hydrogen chloride, chloroformamidine hydrochloride, 1-amidino-1,2,4-triazole hydrochloride, 3,5-dimethylpyrazole-1-carboxamidine nitrate, pyrazole-1-carboxamidine hydrochloride, N-amidinopyrazole-1-carboxamidine hydrochloride, and combinations thereof. Representative examples of suitable guanylating agents that can react with amines through addition reactions include dicyclohexylcarbodiimide, N-ethyl-N'-(3-dimethylaminopropyl)carbodiimide, diisopropylcarbodiimide, diphenylcarbodiimide, cyanamide, and combinations thereof.

Preferred guanylating agents include O-methylisourea sulfate, O-methylisourea hydrogen sulfate, O-methylisourea acetate, O-ethylisourea hydrogen sulfate, O-ethylisourea hydrogen chloride, dicyclohexylcarbodiimide, N-ethyl-N'-(3-dimethylaminopropyl)carbodiimide, diisopropylcarbodiimide, diphenylcarbodiimide, and combinations thereof. Particularly preferred guanylating agents include O-methylisourea sulfate, O-methylisourea acetate, diisopropylcarbodiimide, and combinations thereof. Such guanylating agents are known and can be prepared by known methods. At least some of the guanylating agents are also commercially available.

In another embodiment, the process indicator may comprise, consist essentially of, or even consist of, a crosslinked silylated branched polyethylenimine. Branched silylated polyethylenimine can be prepared, for example, by reaction of an amine-reactive organosilane coupling agent with at least some of the primary amines present in branched PEI resulting in silylated branched PEI. Examples of suitable amine-reactive organosilane coupling agents include compounds represented by the formula:

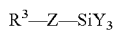

$$R^3-Z-SiY_3$$

wherein $R^3$ and Z are as previously defined, each Y independently represents a hydrolyzable group.

The term "hydrolyzable group", as used herein, denotes a group that can be hydrolyzed, which means it can react with water to provide silanol groups (Si—OH groups) that can further react with groups (e.g., hydroxyl groups) on the surface of the substrate. The hydrolysis and condensation reactions may occur spontaneously and/or in the presence of a hydrolysis/condensation catalyst. Examples of hydrolyzable groups include halide groups, such as chlorine, bromine, iodine or fluorine, alkoxy groups (—OR' wherein R' represents an alkyl group, preferably containing 1 to 6, more preferably 1 to 4 carbon atoms, and which may optionally be substituted by one or more halogen atoms), acyloxy groups (—O—(C═O)—R" wherein R" is as defined for R'), aryloxy groups (—OR'" wherein R'" represents an aryl moiety, preferably containing 6 to 12, more preferably containing 6 to 10 carbon atoms, which may be optionally substituted by one or more substituents independently selected from halogens and $C_1$-$C_4$ alkyl groups which may optionally be substituted by one or more halogen atoms). In the above formulae, R', R", and R'" may include branched structures.

In some embodiments, preferred hydrolyzable groups Y include methoxy and ethoxy groups.

Examples of suitable amine-reactive organosilane coupling agents include: 3-isocyanatopropyltriethoxysilane; 3-isocyanatopropyltrimethoxysilane; 2-isocyanatoethyltriethoxysilane; 2-isocyanatoethyltrimethoxysilane; 3-acryloxypropyltriethoxysilane; 3-acryloxypropyltrimethoxysilane; 2-acryloxyethyltriethoxysilane; 2-acryloxyethyltrimethoxysilane; 3-glycidoxypropyltriethoxysilane; 3-glycidoxypropyltrimethoxysilane; 2-(3,4-epoxycyclohexyl)ethyltrimethoxysilane; and 2-(3,4-epoxycyclohexyl)ethyltriethoxysilane.

In this embodiment, typically, from 5 to 70 percent of the primary amino groups, preferably 10 to 40 percent of the primary amino groups in the PEI are reacted with the silane coupling agent. The reaction is typically carried out in an organic solvent, although water may be present if desired. Upon coating and drying of the silane-functionalized PEI on a substrate, the hydrolyzable groups hydrolyze and form siloxane crosslinks to other silane groups. This results in a crosslinked PEI disposed on the substrate, and depending on the specific substrate, it may be chemically bonded to the substrate (e.g., if the substrate has available hydroxyl groups at its surface; e.g., as in the case of cellulosic paper). Exemplary substrates may include any substrate described herein.

In another embodiment, the synthetic amine-containing compound comprises a polyethylenimine that is chemically bonded to silica.

This may be achieved, for example, by coating an acidified dispersion of silica nanoparticles on a substrate (e.g., cellulosic paper or a substrate as described elsewhere herein), drying to form a silica coating on the substrate. Contacting the silica surface (e.g., by dip coating, spraying, or spin coating) with an amine-reactive silane coupling agent (e.g., 3-acryloxypropyltrimethoxysilane or 3-isocyanatopropyltriethoxyilane or other coupling agents as described herein) cause reaction and functionalization of the silica with amine-reactive groups on its surface. Subsequently contacting the functionalized surface with PEI results in covalent bonding of the PEI to the silica, thereby reducing leaching by recirculating disinfectant. Further details concerning the preparation of acidified silica nanoparticle dispersions and acid-sintered silica coatings prepared thereby can be found, for example, in U.S. Pat. Appl. Publ. Nos. 2015/0232673 (Jing et al.), 2015/0203790 (Strerath et al.), 2015/0252196 (Strerath et al.), and 2015/0246350 (Sun et al.).

Polyethylenimine that is chemically bonded to silica can also be prepared by a multi-step process in which silica particles (e.g., colloidal silica particles) are combined with an amino-functional hydrolyzable silane (e.g., aminopropyltriethoxysilane, aminopropyltrimethoxysilane). The resulting dispersion of amino-functional silica particles is mixed with a second dispersion of a silylated branched polyethylenimine (e.g., preparable as discussed hereinabove). The resulting mixture is then coated onto a substrate and dried.

If desired, polyallylamine (PAA) may be substituted for, or combined with, polyethylenimine in the various embodiments described herein. Polyallylamine can be obtained from commercial sources (e.g., Sigma-Aldrich Corp.) or prepared according to known methods.

The molecular weight of the PAA may be tailored depending on specific application requirements. In some embodiments, the PAA has a molecular weight ($M_W$) of 500 to 5000 g/mole. In some embodiments the PAA has a molecular weight ($M_W$) of 5000 to 15000 g/mole. In some embodiments the PAA has a molecular weight ($M_W$) of 15000 to 30000 g/mole. In some embodiments the PAA has a molecular weight ($M_W$) of 30000 to 60000 g/mole. In some embodiments the PAA has a molecular weight ($M_W$) of 60000 to 100000 g/mole. In some embodiments the PAA has a molecular weight ($M_W$) of greater than or equal to 100000 g/mole.

Any of the synthetic amine-containing compounds described herein may be admixed with an inert film-forming polymeric binder. The film-forming polymeric binder may be provided, for example, as a latex. In some preferred embodiments, the latex and the amine-containing compound are combined prior to depositing the mixture on a substrate. Suitable film-forming polymers include acrylics (e.g., polybutyl acrylate and polymethyl methacrylate), ethylene-vinyl acetate copolymers (and partially or completely hydrolyzed versions thereof, polyvinyl alcohols, polyurethanes, polyamides, polyvinyl chloride, polystyrenes, polyesters, polycarbonates, natural and synthetic rubbers, and combinations thereof The film-forming polymeric binder may be self-crosslinkable.

If present, the inert film-forming polymeric binder is preferably present in an amount of up to 50 percent by weight, more preferably from 1 to 30 percent by weight, and more preferably from 5 to 25 percent by weight, based on the combined total weight of the inert film-forming polymeric binder and the synthetic amine-containing compound(s).

Select Embodiments of the Present Disclosure

In a first embodiment, the present disclosure provides a method of disinfecting a medical device, the method comprising steps:
  a) contacting a disinfectant with a process indicator and the medical device, wherein the disinfectant comprises at least one aldehyde, wherein the process indicator contains a synthetic amine-containing compound disposed on a substrate, wherein the synthetic amine-containing compound is reactive with the disinfectant to form at least one adduct, wherein the synthetic amine-containing compound and the medical device are in fluid communication through the disinfectant, wherein a predetermined disinfectant exposure criterion exists for contacting the disinfectant with the medical device, and wherein the synthetic amine-containing compound comprises at least one of primary amino groups or secondary amino groups; and
  b) spectrally observing the process indicator and obtaining at least one parameter therefrom that is predictive of the predetermined disinfectant exposure criterion; and
  c) determining that the predetermined disinfectant exposure criterion has been achieved.

In a second embodiment, the present disclosure provides a method according to the first embodiment, wherein the synthetic amine-containing compound comprises a synthetic amine-containing polymer.

In a third embodiment, the present disclosure provides a method according to the first or second embodiment, wherein the synthetic amine-containing polymer comprises at least one of:
  i) branched polyethylenimine;
  ii) branched polyethylenimine that has been e-beam grafted to the substrate;
  iii) crosslinked branched polyethylenimine;
  iv) crosslinked branched guanylated polyethylenimine; or
  v) crosslinked branched silylated polyethylenimine.

In a fourth embodiment, the present disclosure provides a method according to the third embodiment, wherein the crosslinked branched silylated polyethylenimine comprises a crosslinked reaction product of a polyethylenimine with a compound containing at least two amine-reactive (e.g., acryl, epoxy, vinylsulfonyl, —C(=O)H, and/or isocyanato) groups.

In a fifth embodiment, the present disclosure provides a method according to the second embodiment, wherein the synthetic amine-containing polymer comprises an amine-functional polysiloxane.

In a sixth embodiment, the present disclosure provides a method according to the first embodiment, wherein the synthetic amine-containing compound comprises a polyethylenimine that is chemically bonded to silica.

In a seventh embodiment, the present disclosure provides a method according to any one of the first to sixth embodiments, wherein the disinfectant comprises at least one dialdehyde.

In an eighth embodiment, the present disclosure provides a method according to any one of the first to seventh embodiments, wherein the disinfectant comprises at least one of glutaraldehyde or ortho-phthalaldehyde.

In a ninth embodiment, the present disclosure provides a method according to any one of the first to eighth embodiments, wherein the synthetic amine-containing compound is admixed with an inert polymeric binder.

In a tenth embodiment, the present disclosure provides a method according to any one of the first to ninth embodiments, wherein the predetermined disinfectant exposure criterion corresponds to an industry recognized standard for disinfection of the medical device.

In an eleventh embodiment, the present disclosure provides a method according to any one of the first to tenth embodiments, wherein the medical device comprises an endoscope having at least one interior conduit, and wherein the disinfectant is recirculated through the at least one interior conduit.

In a twelfth embodiment, the present disclosure provides a method according to any one of the first to eleventh embodiments, wherein the at least one parameter comprises optical reflectance.

In a thirteenth embodiment, the present disclosure provides a method according to any one of the first to twelfth embodiments, wherein the at least one parameter comprises a visible color.

In a fourteenth embodiment, the present disclosure provides a method according to any one of the first to thirteenth embodiments, wherein the at least one process parameter indicator is continuously obtained.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight. Examples indicated by a "PI" prefix (e.g., PI1, PI20, etc.) are examples that are included to show process indicator configurations capable of being used in practice of the present disclosure, but not necessarily working examples of the entire process described herein. In the examples below, the symbol "#" means number, and the symbol "%" means percent. Unless otherwise specified, experiments were carried out under ambient conditions (e.g., temperature, pressure, humidity).

| TABLE OF REAGENTS | |
|---|---|
| Branched polyethylenimine (MW 60K g/mole, 50 wt. % in water) | Thermo Fisher Scientific, Waltham, Massachusetts |
| Branched polyethylenimine (MW 50-100K g/mole, 30 wt. % in water) | Polysciences, Inc., Warrington, Pennsylvania |
| Branched polyethylenimine (MW 25K g/mole, cat# 408727) | Sigma-Aldrich Corp., St. Louis, Missouri |
| Branched polyethylenimine (MW 800 g/mole, cat# 408719) | Sigma-Aldrich Corp. |
| Polyethylenimine (80% ethoxylated, 37 wt. % in water, MW 50K) | Sigma-Aldrich Corp. |
| Polyallylamine (MW 65 K g/mole, 10 wt. % in water) | Sigma-Aldrich Corp. |
| 3-(Acryloxypropyl)trimethoxysilane (AS) | Gelest, Inc., Morrisville, Pennsylvania |
| 3-Glycidoxypropyltrimethoxysilane (GPS) | Gelest, Inc. |
| PZ-28 polyfunctional aziridine | PolyAziridine LLC., Medford, New Jersey |
| Diethyl glutaconate | Sigma-Aldrich Corp. |
| Butanediol diglycidyl ether (BUDGE) | Sigma-Aldrich Corp. |
| Poly(ethylene glycol) diglycidyl ether ($M_n$ 500 g/mole, cat# 475696) | Sigma-Aldrich Corp. |
| SR454 (3 mole ethoxylated trimethylolpropane triacrylate) | Sartomer Corp., Exton, Pennsylvania |
| SR415 (20 mole ethoxylated trimethylolpropane triacrylate) | Sartomer Corp. |
| INCOREZ CS8057 polyurethane dispersion | Incorez Ltd., Lancashire, England |
| NEOREZ R966 polyurethane dispersion (R966) | DSM Corp., Elgin, Illinois |
| NEOCRYL A612 polyacrylic dispersion (A612) | DSM Corp. |
| POVAL 49-88 polyvinyl alcohol | Kuraray Ltd., Singapore |
| Polyvinyl pyrrolidone K90, MW 360K g/mole | Sigma-Aldrich Corp. |
| Nalco 1115 aqueous silica nanoparticle dispersion (spherical, 4 nm) | Nalco Co., Naperville, Illinois |
| 3-aminopropyltriethoxysilane and 3-aminopropyltrimethoxysilane | Sigma-Aldrich Corp. |
| IRGACURE 184 (1-hydroxy-cyclohexyl) phenyl ketone | BASF Corp., Florham Park, New Jersey |
| ortho-phthalaldehyde (RAPICIDE OPA/28) | Medivators, Inc., Minneapolis, Minnesota |
| RAPICIDE GLUT (2.5% glutaraldehyde) | Medivators, Inc. |

Example PI1

Branched polyethylenimine (MW 50,000-100,000 g/mole as a 30 wt. % solution in water, available from Polysciences Inc.) was coated onto a nylon 6,6 membrane (single reinforced layer nylon three zone membrane with nominal pore size of 1.8 microns, #080ZN, obtained from 3M Purification Inc., Meriden, Conn.) with a #10 Meyer rod. The coated substrate was then dried in a vacuum oven at 60° C. for 2-3 hours. The dried sample was cut into test strips (20 mm by 50 mm). The coated surface of the test strips was white in color.

Individual testing solutions of ortho-phthalaldehyde (abbreviation OPA, Medivators Inc.) in water were prepared at concentrations of 0.2 wt. %, 0.275 wt. % and 0.575 wt. % OPA. Test strips were evaluated by immersing a test strip in an OPA testing solution bath and maintaining the test strip immersed in the bath for varying periods of time (3, 5, 7, 9, 11, 13, 15, 17, 19, or 21 minutes). Following immersion for the designated period of time, the test sample was removed from the testing solution, immersed in a fresh bath of distilled water for 5 minutes, and then rinsed with isopropyl alcohol for about 5 seconds. The rinsed samples were air dried. The optical density of each test strip was measured using an X-Rite Series 500 spectrodensitometer with measurements taken between 400 and 700 nm (X-Rite Inc., Grand Rapids, Mich.). For each combination of OPA concentration and sample immersion time a total of three measurements were made. The mean optical density values obtained are reported in Table 1, below.

TABLE 1

| Immersion Time, | Mean Optical Density Measurement Based on OPA Concentration | | |
|---|---|---|---|
| minutes | 0.2 wt. % OPA | 0.275 wt. % OPA | 0.575 wt. % OPA |
| 3 | 0.03 | 0.03 | 0.10 |
| 5 | 0.04 | 0.07 | 0.20 |
| 7 | 0.04 | 0.10 | 0.31 |
| 9 | 0.06 | 0.11 | 0.26 |
| 11 | 0.06 | 0.17 | 0.32 |
| 13 | 0.10 | 0.25 | 0.28 |
| 15 | 0.12 | 0.25 | 0.38 |
| 17 | 0.18 | 0.23 | 0.42 |
| 19 | 0.24 | 0.39 | 0.46 |
| 21 | 0.21 | 0.32 | 0.42 |

Example PI2

Branched polyethylenimine (MW 50,000-100,000 g/mole as a 30 wt. % solution in water) was coated onto Whatman 410 filter paper with a #24 Meyer rod (RD Specialties, Webster, N.Y.). The coated substrate was then dried in a vacuum oven at 60° C. for 2-3 hours. The dried sample was cut into test strips (20 mm by 50 mm). The coated surface of the test strips was white in color.

Individual testing solutions of OPA in water were prepared at concentrations of 0.2 wt. %, 0.35 wt. % and 0.575 wt. % OPA. Test strips were evaluated by immersing a test strip in an OPA testing solution bath and maintaining the test strip immersed in the bath for varying periods of time (5, 10, or 15 minutes). Following immersion for the designated period of time, the test sample was removed from the testing solution, immersed in a fresh bath of distilled water for 15 minutes, and then rinsed with isopropyl alcohol for about 5 seconds. The rinsed samples were air dried. The color of the test strips was determined by visual inspection. Results are reported in Table 2, below.

TABLE 2

| Immersion Time | Visual Appearance of Test Strip | | |
|---|---|---|---|
| (min) | 0.2 wt. % OPA | 0.35 wt. % OPA | 0.575 wt. % OPA |
| 5 | white | white | yellow |
| 10 | white | pale yellow | yellow |
| 15 | white | yellow | dark orange |

Example PI3

A 50:50 viscose/felt nonwoven material (70 gsm, 1.4 mm thick, obtained from Fibertex Nonwovens, Ingleside, Ill.) was immersed in a bath containing branched polyethylenimine (MW 50,000-100,000 g/mole as a 30 wt. % solution in water) and subsequently agitated by rotational mixing for about 2 hours. The nonwoven material was removed from the bath and dried in a vacuum oven at 60° C. for 2-3 hours. The dried material was cut into test samples (12.5 mm by 12.5 mm). The test samples were immersed in a bath of 1% INTERCEPT detergent (Medivators, Inc.) for 7.5 minutes followed by immersion in a fresh distilled water bath for an additional 7.5 minutes. The samples were air dried. The test sample was white in color.

Individual testing solutions of OPA in water were prepared at concentrations of 0.2 wt. %, 0.35 wt. % and 0.575 wt. % OPA. Test samples were evaluated by immersing a test sample in an OPA testing solution bath and maintaining the test strip immersed in the bath for 5 minutes. Following immersion for the designated period of time, the test sample was removed from the testing solution, immersed in a fresh bath of distilled water for 15 minutes, and then rinsed with isopropyl alcohol for about 5 seconds. The rinsed samples were air dried. Each test sample was evaluated for color change by visual examination. The test sample immersed in 0.2 wt. % OPA displayed a pale yellow color over about 30% of the sample surface. The test sample immersed in 0.35 wt. % OPA displayed a yellow color over about 60% of the sample surface. The test sample immersed in 0.575 wt. % OPA displayed a yellow color over about 90% of the sample surface.

Example PI4

A substrate material was prepared by laminating a polyester/SURLYN film (about 2.5 mil thick) onto one side of Whatman 410 Grade filter paper (about 7.3 mil thick). The paper side of the substrate was coated with polyallylamine (MW 65,000 g/mole as a 10 wt. % solution in water, available from Sigma-Aldrich Corporation) using a #18 Meyer rod. The coated material was then dried at 100° C. for 5 minutes. The coating and drying procedures were repeated two additional times to provide a triple coated material. The dried sample was cut into test strips (25.4 mm by 50.8 mm). The coated surface of the test strips was white in color A testing solution of ortho-phthalaldehyde (OPA) was prepared at a concentration of 0.575 wt. % OPA. A test strip was evaluated by immersing the test strip in an OPA testing solution bath and maintaining the test strip immersed in the bath for 5 minutes. Following immersion the test strip was removed from the testing solution, immersed in a fresh bath of distilled water for 5 minutes, and then rinsed with isopropyl alcohol for about 5 seconds. The rinsed sample was air dried and then evaluated for color change by visual examination. The test strip immersed in 0.575 wt. % OPA displayed a color change from white (prior to immersion) to yellow (post-immersion).

Example PI5

Branched polyethylenimine (MW 60,000 g/mole as a 50 wt. % solution in water, available from Thermo Fisher Scientific, Waltham, Massachusetts) was diluted to 10 wt. % with added distilled water. This solution was coated onto the paper side of the substrate material described in Example PI4 using reverse gravure printing. The coated substrate was then dried at 100° C. for 5 minutes. The dried sample was cut into test strips (20 mm by 50 mm).

Individual testing solutions of ortho-phthalaldehyde (OPA) in water were prepared at concentrations of 0.09 wt. %, and 0.35 wt. % OPA. Test strips were evaluated by immersing a test strip in an OPA testing solution bath according to one of the following evaluation Protocols A-D. For Protocol-A a test strip was immersed for 5 minutes in the 0.35 wt. % OPA bath with the bath temperature maintained at 25° C. For Protocol-B a test strip was immersed for 1.35 minutes in the 0.35 wt. % OPA bath with the bath temperature maintained at 25° C. For Protocol-C a test strip was immersed for 5 minutes in the 0.09 wt. % OPA bath with the bath temperature maintained at 25° C. For Protocol-D a test strip was immersed for 5 minutes in the 0.35 wt. % OPA bath with the bath temperature maintained at 10° C. For each of the Protocols A-D, following immersion for the designated period of time, the test sample was removed from the testing solution, rinsed with distilled water for 15 minutes, and then rinsed with isopropyl alcohol for about 5 seconds. The rinsed samples were air dried for approximately 10 seconds. The reflectance measurement of each test strip was determined at an emitted wavelength of 450 nm using an X-Rite eXact NGH Handheld Spectrophotometer with a 1.5 mm aperture (X-Rite Inc., Grand Rapids, Mich.). The mean reflectance values (n=18) for Protocols A-D are reported in Table 3. In Table 4, the mean reflectance values (n=18) using Protocol A and Protocol B at emitted wavelengths ranging from 450 nm to 550 nm are reported.

TABLE 3

|  | wt. % OPA | Bath Temperature, ° C. | Immersion Time, minutes | Reflectance, % |
| --- | --- | --- | --- | --- |
| Protocol-A | 0.35 | 25 | 5 | 18 |
| Protocol-B | 0.35 | 25 | 1.35 | 51 |
| Protocol-C | 0.09 | 25 | 5 | 61 |
| Protocol-D | 0.35 | 10 | 5 | 46 |

TABLE 4

|  | Reflectance, % | |
| --- | --- | --- |
|  | Protocol A | Protocol B |
| 450 nm | 18 | 51 |
| 460 nm | 25 | 61 |
| 470 nm | 34 | 65 |
| 480 nm | 42 | 68 |
| 490 nm | 49 | 73 |
| 500 nm | 54 | 76 |
| 510 nm | 58 | 78 |
| 520 nm | 60 | 79 |
| 530 nm | 63 | 80 |
| 540 nm | 65 | 81 |
| 550 nm | 68 | 82 |

Example PI6

Branched polyethylenimine (MW 60,000 g/mole as a 50 wt. % solution in water) was diluted to 10 wt. % with added distilled water. This solution was coated onto the paper side of the substrate material described in Example PI4 using reverse gravure printing. The coated substrate was then dried at 100° C. for 5 minutes. The dried sample was cut into test strips (20 mm by 50 mm).

Individual testing solutions of ortho-phthalaldehyde (OPA) in water were prepared at concentrations of 0.09 wt. %, and 0.35 wt. % OPA. Test strips were evaluated by immersing a test strip in an OPA testing solution bath according to one of the following evaluation Protocols A-C (described in Example PI5). In this example, prior to exposure of the samples to OPA according to any of protocols A-C, the samples were soaked in a 1/400 w/w dilution of Intercept detergent (Medivators) in distilled water, followed by 5 minutes soaking in water. For each of the Protocols A-C, following immersion for the designated period of time, the test sample was removed from the testing solution, rinsed with distilled water for 15 minutes, and then rinsed with isopropyl alcohol for about 5 seconds. The rinsed samples were air dried for approximately 10 seconds. The reflectance measurement of each test strip was determined at an emitted wavelength of 450 nm using an X-Rite eXact NGH Handheld Spectrophotometer with a 1.5 mm aperture (X-Rite Inc.). The mean reflectance values (n=18) for Protocols A-C are reported in Table 5, below.

TABLE 5

|  | wt. % OPA | Bath Temperature, ° C. | Immersion Time, minutes | Reflectance, % |
| --- | --- | --- | --- | --- |
| Protocol-A | 0.35 | 25 | 5 | 13 |
| Protocol-B | 0.35 | 25 | 1.35 | 39 |
| Protocol-C | 0.09 | 25 | 5 | 38 |

Example PI7

Branched polyethylenimine (MW 50,000-100,000 g/mole as a 30 wt. % solution in water) was diluted to 10 wt. % with added distilled water. This solution was coated onto the paper side of the substrate material described in Example PI4 using a #18 Meyer rod. The coated material was then washed by immersion in MilliQ water (EMD Millipore, Billerica, Mass.) for 5 minutes with gentle agitation. The coated material was removed from the wash solution and dried at 110° C. for about 5 minutes. The dried sample was cut into test strips (20 mm by 50 mm).

Test strips were evaluated by immersing a test strip in a bath containing 1.5% glutaraldehyde disinfectant solution (prepared using RAPICIDE GLUT available from Medivators Inc.). The bath temperature was maintained at 35° C. and test strips were immersed for either 1.7 minutes or 5 minutes. Following immersion for the designated period of time, each test sample was removed from the testing solution, rinsed with distilled water for 5 minutes, and then rinsed with isopropyl alcohol for about 5 seconds. The rinsed samples were air dried. The reflectance measurement of each test strip was determined at an emitted wavelength of 510 nm using an X-Rite eXact NGH Handheld Spectrophotometer with a 1.5 mm aperture (X-Rite Inc.). The mean reflectance values (n=9) for different test procedures (i.e., wash method A or B, and bath immersion time) are reported in Table 6, below.

TABLE 6

| Immersion Time, minutes | Reflectance, % |
| --- | --- |
| 1.7 | 56 |
| 5 | 48 |

Example PI8

Branched polyethylenimine (MW 60,000 g/mole as a 50 wt. % solution in water) was diluted to 10 wt. % with added distilled water. The pH of the diluted solution was adjusted to pH=5 by the addition of concentrated hydrochloric acid. This solution was coated onto the paper side of the substrate material described in Example PI4 using a #18 Meyer rod. The coated substrate was then dried at 100° C. for 5 minutes. The dried sample was cut into test strips (20 mm by 50 mm).

Individual testing solutions of ortho-phthalaldehyde (OPA) in water were prepared at concentrations of 0.10 wt. %, and 0.35 wt. % OPA. Test strips were evaluated by immersing a test strip in an OPA testing solution bath according to one of the following evaluation Protocols E-I. For Protocol-E a test strip was immersed for 1 minute in the 0.35 wt. % OPA bath with the bath temperature maintained at 30° C. For Protocol-F a test strip was immersed for 1.35 minutes in the 0.35 wt. % OPA bath with the bath temperature maintained at 25° C. For Protocol-G a test strip was immersed for 1.62 minutes in the 0.35 wt. % OPA bath with the bath temperature maintained at 20° C. For Protocol-H a test strip was immersed for 5 minutes in the 0.10 wt. % OPA bath with the bath temperature maintained at 25° C. For Protocol-I a test strip was immersed for 5 minutes in the 0.35 wt. % OPA bath with the bath temperature maintained at 25° C. For each of the Protocols E-I, following immersion for the designated period of time, the test sample was removed from the testing solution, rinsed with distilled water for 5 minutes, and then rinsed with isopropyl alcohol for about 5 seconds. The rinsed samples were air dried. The reflectance measurement of each test strip was determined at an emitted wavelength of 500 nm using an X-Rite eXact NGH Handheld Spectrophotometer with a 1.5 mm aperture (X-Rite Inc.). The mean reflectance values (n=6) for Protocols E-I are reported in Table 7, below.

TABLE 7

| | wt. % OPA | Bath Temperature, ° C. | Immersion Time, minutes | Reflectance, % |
|---|---|---|---|---|
| Protocol-E | 0.35 | 30 | 1 | 74 |
| Protocol-F | 0.35 | 25 | 1.35 | 67 |
| Protocol-G | 0.35 | 20 | 1.62 | 75 |
| Protocol-H | 0.10 | 25 | 5 | 78 |
| Protocol-I | 0.35 | 25 | 5 | 42 |

Example PI9

Branched polyethylenimine (MW 50,000-100,000 g/mole as a 30 wt. % solution in water) was diluted to 5 wt. % with added isopropyl alcohol. A 20 g portion of the diluted polymer sample was combined with the crosslinker compound butanediol diglycidyl ether (abbreviation "BUDGE", 0.026 mL). The two components were mixed together for 5 minutes using a roller mill assembly (model #88881003, Thermo Fisher Scientific) and the resulting product was coated onto the paper side of the substrate material described in Example PI4 using a #18 Meyer rod. The coated samples were dried at room temperature for about 30 minutes.

Example PI10

The procedure of Example PI9 was followed, except that in order to achieve a greater amount of polymer crosslinking, 0.053 mL of BUDGE was used instead of 0.026 mL.

Example PI11

The procedure of Example PI9 was followed, except that in order to achieve a greater amount of polymer crosslinking, 0.079 mL of BUDGE was used instead of 0.026 mL.

Example PI12

Branched polyethylenimine (MW 50,000-100,000 g/mole as a 30 wt. % solution in water) was diluted to 10 wt. % with added isopropyl alcohol. A 20 g portion of the diluted polymer sample was combined with the crosslinker BUDGE (0.053 mL). The two components were mixed together for 5 minutes using a roller mill assembly (model #88881003, Thermo Fisher Scientific,) and the resulting product was coated onto the paper side of the substrate material described in Example PI4 using a #18 Meyer rod. The coated samples were dried at room temperature for about 30 minutes.

Example PI13

The procedure of Example PI12 was followed, except that in order to achieve a greater amount of polymer crosslinking, 0.105 mL of BUDGE was used instead of 0.053 mL.

Example PI14

The procedure of Example PI12 was followed, except that in order to achieve a greater amount of polymer crosslinking, 0.158 mL of BUDGE was used instead of 0.053 mL.

Example PI15

Branched polyethylenimine (MW 50,000-100,000 g/mole as a 30 wt. % solution in water) was diluted to 15 wt. % with added isopropyl alcohol. A 20 g portion of the diluted polymer sample was combined with the crosslinker BUDGE (0.079 mL). The two components were mixed together for 5 minutes using a roller mill assembly (model #88881003, Thermo Fisher Scientific) and the resulting product was coated onto the paper side of the substrate material described in Example PI4 using a #18 Meyer rod. The coated samples were dried at room temperature for about 30 minutes.

Example PI16

The procedure of Example PI15 was followed, except that in order to achieve a greater amount of polymer crosslinking, 0.158 mL of BUDGE was used instead of 0.079 mL.

Example PI17

Branched polyethylenimine (MW 50,000-100,000 g/mole as a 30 wt. % solution in water) was diluted to 20 wt. % with added isopropyl alcohol. A 20 g portion of the diluted polymer sample was combined with the crosslinker BUDGE (0.105 mL). The two components were mixed together for 5 minutes using a roller mill assembly (model #88881003, Thermo Fisher Scientific) and the resulting product was coated onto the paper side of the substrate material described in Example PI4 using a #18 Meyer rod. The coated samples were dried at room temperature for about 30 minutes.

The coated materials from Examples PI9 to PI15 were washed by immersion in MILLIQ water (EMD Millipore) for 5 minutes with gentle agitation, removed from the wash solution and then dried at 110° C. for about 5 minutes. The dried samples were white in color. Test strips (20 mm by 50 mm) were prepared.

A testing solution of ortho-phthalaldehyde (OPA) in water was prepared at a concentration of 0.35 wt. % OPA. Test strips from Examples PI12, PI13, and PI17 were evaluated by immersing a test strip in the OPA testing solution bath and maintaining the test strip immersed in the bath for varying periods of time (1.7 and 5 minutes). Following immersion for the designated period of time, the test strip was removed from the testing solution, immersed in a fresh bath of distilled water for 15 minutes, and then rinsed with isopropyl alcohol for about 5 seconds. The rinsed samples were air dried. The reflectance measurement of each test strip was determined at an emitted wavelength 470 nm using an X-Rite eXact NGH Handheld Spectrophotometer with a 1.5 mm aperture (X-Rite Inc.). The mean reflectance values (n=10) for Examples PI12, PI13, and PI17 are reported in Table 8, below.

TABLE 8

| | Mean Reflectance, %, Values following Immersion in 0.35% OPA | |
|---|---|---|
| Example | 1.7 minutes | 5 minutes |
| PI12 | 63 | 37 |
| PI13 | 58 | 29 |
| PI17 | 55 | 29 |

Example PI18

Branched polyethylenimine (MW 60,000 g/mole as a 50 wt. % solution in water) was diluted to 5 wt. % with distilled water. A 20 g portion of the diluted polymer sample was combined with the crosslinker compound poly(ethylene glycol) diglycidyl ether (abbreviation "diepoxy PEG", $M_n$=500 g/mole, 0.026 mL, Sigma-Aldrich Corporation). The two components were mixed together for 10 minutes using a roller mill assembly (model #88881003, Thermo Fisher Scientific) and the resulting product was coated onto the paper side of the substrate material described in Example PI4 using a #16 Meyer rod. The coated samples were dried at 100° C. for about 10 minutes.

Example PI19

The procedure of Example PI18 was followed, except that in order to achieve a greater amount of polymer crosslinking, 0.053 mL of diepoxy PEG was used instead of 0.026 mL.

Example PI20

The procedure of Example PI18 was followed, except that in order to achieve a greater amount of polymer crosslinking, 0.079 mL of diepoxy PEG was used instead of 0.026 mL.

Example PI21

Branched polyethylenimine (MW 60,000 g/mole as a 50 wt. % solution in water) was diluted to 10 wt. % with added isopropyl alcohol. A 20 g portion of the diluted polymer sample was combined with the crosslinker diepoxy PEG (0.053 mL). The two components were mixed together for 5 minutes using a roller mill assembly (model #88881003, Thermo Fisher Scientific) and the resulting product was coated onto the paper side of the substrate material described in Example PI4. The coated samples were dried at 100° C. for about 10 minutes.

Example PI22

The procedure of Example PI21 was followed, except that in order to achieve a greater amount of polymer crosslinking, 0.105 mL of diepoxy PEG was used instead of 0.053 mL.

Example PI23

The procedure of Example PI21 was followed, except that in order to achieve a greater amount of polymer crosslinking, 0.158 mL of diepoxy PEG was used instead of 0.053 mL.

Example PI24

Branched polyethylenimine (MW 60,000 g/mole as a 50 wt. % solution in water) was diluted to 15 wt. % with added isopropyl alcohol. A 20 g portion of the diluted polymer sample was combined with the crosslinker diepoxy PEG (0.079 mL). The two components were mixed together for 5 minutes using a roller mill assembly (model #88881003, Thermo Fisher Scientific) and the resulting product was coated onto the paper side of the substrate material described in Example P14 using a #16 Meyer rod. The coated samples were dried at 100° C. for about 10 minutes.

Example PI25

The procedure of Example PI24 was followed, except that in order to achieve a greater amount of polymer crosslinking 0.158 mL of diepoxy PEG was used instead of 0.079 mL.

Example PI26

Branched polyethylenimine (MW 60,000 g/mole as a 50 wt. % solution in water) was diluted to 20 wt. % with added isopropyl alcohol. A 20 g portion of the diluted polymer sample was combined with the crosslinker diepoxy PEG (0.105 mL). The two components were mixed together for 5 minutes using a roller mill assembly (model #88881003, Thermo Fisher Scientific) and the resulting product was coated onto the paper side of the substrate material described in Example P14 using a #16 Meyer. The coated samples were dried at 100° C. for about 10 minutes.

Example PI27

Branched polyethylenimine (MW 60,000 g/mole as a 50 wt. % solution in water) (21.45 g) and distilled water (45 mL) were combined. O-methyl isourea hemisulfate (7.66 g, Sigma-Aldrich Corporation) was then added and the reaction was stirred for about 15 hours. Heptane (120 mL) was added followed by the addition of BUDGE (2.4 mL) with rapid stirring. After stirring for an additional 3 hours, the solvent was decanted from the reaction mixture. Isopropyl alcohol (200 mL) was added to the flask and the mixture was heated to reflux temperature with rapid stirring. The solid was removed by filtration and subjected to two more cycles of isopropyl alcohol washing. After the final washing procedure, the resulting solid was isolated by filtration, dried under vacuum, and then crushed to provide the cross-linked guanylated polyethylenimine as a white powder.

A sample of the cross-linked guanylated polyethylenimine (500 mg) was added to a glass vial followed by the addition of 1 mL of 0.575 wt. % OPA solution. Upon addition of the OPA, the powder immediately turned from an initial white color to a bright yellow color.

Example PI28

Branched polyethylenimine (MW 60,000 g/mole as a 50 wt. % solution in water) (21.45 g) and distilled water (45 mL) were combined in a round bottom flask. A solution containing Rhodamine B isothiocyanate (1 mg, Sigma-Aldrich Corporation) dissolved in distilled water (10 mL) was added to the flask and the reaction was stirred for 15 minutes. O-methyl isourea hemisulfate (7.66 g) was then added and the reaction was stirred for about 15 hours. Heptane (120 mL) was added followed by the addition of BUDGE (2.4 mL) with rapid stirring. After stirring for an additional 3 hours, the solvent was decanted from the reaction mixture. Isopropyl alcohol (200 mL) was added to the flask and the mixture was heated to reflux temperature with rapid stirring. The solid was removed by filtration and subjected to two more cycles of isopropyl alcohol washing. After the final washing procedure, the resulting pale pink solid was isolated by filtration, dried under vacuum, and then crushed to provide a powder of the cross-linked guanylated polyethylenimine labeled with 0.01% rhodamine.

A sample of the cross-linked guanylated polyethylenimine labeled with 0.01% rhodamine (500 mg) was added to a glass vial followed by the addition of 1 mL of 0.575 wt. % OPA solution. Upon addition of the OPA, the powder turned from an initial pale pink color to a bright yellow color after 5 minutes.

Example PI29

Branched polyethylenimine (MW 60,000 g/mole as a 50 wt. % solution in water) (21.45 g) and distilled water (45 mL) were combined in a round bottom flask. A solution containing Rhodamine B isothiocyanate (10 mg, Sigma-Aldrich Corporation) dissolved in distilled water (10 mL) was added to the flask and the reaction was stirred for 15 minutes. O-methyl isourea hemisulfate (7.66 g) was then added and the reaction was stirred for about 15 hours. Heptane (120 mL) was added followed by the addition of BUDGE (2.4 mL) with rapid stirring. After stirring for an additional 3 hours, the solvent was decanted from the reaction mixture. Isopropyl alcohol (200 mL) was added to the flask and the mixture was heated to reflux temperature with rapid stirring. The solid was removed by filtration and subjected to two more cycles of isopropyl alcohol washing. After the final washing procedure, the resulting pink solid was isolated by filtration, dried under vacuum, and then crushed to provide a powder of the cross-linked guanylated polyethylenimine labeled with 0.1% rhodamine.

A sample of the cross-linked guanylated polyethylenimine labeled with 0.1% rhodamine (500 mg) was added to a glass vial followed by the addition of 1 mL of 0.575 wt. % OPA solution. Upon addition of the OPA, the powder turned from an initial pink color to a bright orange color after 5 minutes.

Example PI30

Branched polyethylenimine (MW 50,000-100,000 g/mole as a 30 wt. % solution in water) was diluted to 10 wt. % with added distilled water. This solution was coated onto the paper side of the substrate material described in Example PI4 using reverse gravure printing. The coated substrate was then dried at 100° C. for 5 minutes. Sections of the sample were then treated with e-beam irradiation (10 Mrad with an accelerating voltage of 300 keV). The treated sample was cut into test strips (20 mm by 50 mm).

A testing solution of ortho-phthalaldehyde (OPA) in water was prepared at a concentration of 0.35 wt. % OPA. Test strips were evaluated by immersing a test strip in an OPA testing solution bath and maintaining the test strip immersed in the bath for either 1.7 minutes or 5 minutes. The bath temperature was set at 25° C. Prior to exposure of the test strips to the OPA bath, the strips in distilled water for 4 minutes, and then dried at 100° C. for 8 minutes. Following immersion for the designated period of time, the test sample was removed from the testing solution, rinsed with distilled water for 15 minutes, and then rinsed with isopropyl alcohol for about 5 seconds. The rinsed samples were air dried for approximately 10 seconds. The reflectance measurement of each test strip was determined at an emitted wavelength of 470 nm using an X-Rite eXact NGH Handheld Spectrophotometer with a 1.5 mm aperture (X-Rite Inc.). The mean reflectance values (n=10) are reported in Table 9.

TABLE 9

| wt. % OPA | Bath Temperature, ° C. | Immersion Time, minutes | Reflectance, % |
|---|---|---|---|
| 0.35 | 25 | 5 | 32 |
| 0.35 | 25 | 1.7 | 50 |

Example PI31

Branched polyethylenimine (MW 25,000 g/mole, available from Sigma-Aldrich Corporation (cat #408727) and diluted to a 3 wt. % aqueous solution, abbreviation of "bPEI") was mixed with a 3 wt. % aqueous solution of 3-(acryloxypropyl)trimethoxysilane (abbreviation of "AS", Gelest Inc., Morrisville, Pa.) in a ratio of 4:1 by weight bPEI:AS to form Solution A. NEOCRYL A612 (abbreviation of "A612", DSM Corporation, Elgin, Ill.) was diluted with distilled water to prepare a 3 wt. % solution (Solution B). Solutions A and B were then mixed together in a ratio of 2:3 by weight Solution A:Solution B to form the final coating formulation. A sample of filter paper (Whatman 410) was dip coated with the coating formulation and then dried at 80° C. for 3 minutes. The dried sample was cut into test strips (20 mm by 40 mm). The coated surface of the test strips was white in color.

Individual testing solutions of ortho-phthalaldehyde (OPA) in water were prepared at concentrations of 0.10 wt. %, and 0.35 wt. % OPA. The test strips were evaluated by immersing a test strip into a bath of the OPA testing solution for 5 minutes with the bath temperature maintained at 25° C. The test strip was removed from the bath and checked for a color change by visual examination. In addition, test strips were evaluated to determine if any indicator color from a test strip leached into the OPA bath. For this test a new test strip was immersed and maintained in a fresh OPA bath (0.35 wt. % at 25° C.) for 30 minutes. The bath contained the minimum amount of OPA to fully cover the test strip (typically 1-2 mL). The test strip was then removed from the bath and the bath liquid was checked for color change by visual examination (no leaching=colorless bath, leaching=change in bath color from colorless to either a pale yellow or yellow color). The results are reported in Table 10.

Example PI32

The procedure of Example PI31 was followed, except that Solutions A and B were mixed together in a ratio of 1:1 by weight Solution A: Solution B to form the final coating formulation. The results are reported in Table 10.

Example PI33

The procedure of Example PI31 was followed, except that Solutions A and B were mixed together in a ratio of 3:2 by weight Solution A:Solution B to form the final coating formulation. The results are reported in Table 10.

Example PI34

Branched polyethylenimine (MW 25,000 g/mole, available from Sigma-Aldrich Corporation (cat #408727) and diluted to a 3 wt. % aqueous solution) was mixed with a 3 wt. % aqueous solution of 3-(acryloxypropyl)trimethoxysilane (abbreviation of "AS", Gelest Inc.) in a ratio of 7:3 by weight bPEI:AS to form Solution C. A612 was diluted with distilled water to prepare a 3 wt. % solution (Solution D). Solutions C and D were then mixed together in a ratio of 1:9 by weight Solution C: Solution D to form the final coating formulation. A sample of filter paper (Whatman 410) was dip coated with the coating formulation and then dried at 80° C. for 3 minutes. The dried sample was cut into test strips (20 mm by 40 mm). The coated surface of the test strips was white in color. The test strips were evaluated for color change and color leaching according to the procedure described in Example PI31. The results are reported in Table 10.

Example PI35

The procedure of Example PI34 was followed, except that Solutions C and D were mixed together in a ratio of 2:3 by weight Solution C:Solution D to form the final coating formulation. The results are reported in Table 10.

Example PI36

The procedure of Example PI34 was followed, except that Solutions C and D were mixed together in a ratio of 1:1 by weight Solution C:Solution D to form the final coating formulation. The results are reported in Table 10.

Example PI37

The procedure of Example PI34 was followed, except that Solutions C and D were mixed together in a ratio of 3:2 by weight Solution C:Solution D to form the final coating formulation. The results are reported in Table 10.

Example PI38

Branched polyethylenimine (MW 25,000 g/mole, available from Sigma-Aldrich Corporation (cat #408727) and diluted to a 3 wt. % aqueous solution) was mixed with a 3 wt. % aqueous solution of 3-(acryloxypropyl)trimethoxysilane in a ratio of 3:2 by weight bPEI:AS to form Solution E. A612 was diluted with distilled water to prepare a 3 wt. % solution (Solution F). Solutions E and F were then mixed together in a ratio of 2:3 by weight Solution E:Solution F to form the final coating formulation. A sample of filter paper (Whatman 410) was dip coated with the coating formulation and then dried at 80° C. for 3 minutes. The dried sample was cut into test strips (20 mm by 40 mm). The coated surface of the test strips was white in color. The test strips were evaluated for color change and color leaching according to the procedure described in Example PI31. The results are reported in Table 10.

Example PI39

The procedure of Example PI38 was followed, except that Solutions E and F were mixed together in a ratio of 1:1 by weight Solution E:Solution F to form the final coating formulation. The results are reported in Table 10.

Example PI40

The procedure of Example PI38 was followed, except that Solutions E and F were mixed together in a ratio of 3:2 by weight Solution E:Solution F to form the final coating formulation. The results are reported in Table 10.

Example PI41

Branched polyethylenimine (MW 25,000 g/mole, available from Sigma-Aldrich Corporation (cat #408727) and diluted to a 3 wt. % aqueous solution) was mixed with a 3 wt. % aqueous solution of 3-(acryloxypropyl)trimethoxysilane in a ratio of 1:1 by weight bPEI:AS to form Solution G. A612 was diluted with distilled water to prepare a 3 wt. % solution (Solution H). Solutions G and H were then mixed together in a ratio of 1:9 by weight Solution G: Solution H to form the final coating formulation. A sample of filter paper (Whatman 410) was dip coated with the coating formulation and then dried at 80° C. for 3 minutes. The dried sample was cut into test strips (20 mm by 40 mm). The coated surface of the test strips was white in color. The test strips were evaluated for color change and color leaching according to the procedure described in Example PI31. The results are reported in Table 10.

Example PI42

Branched polyethylenimine (MW 25,000 g/mole, available from Sigma-Aldrich Corporation (cat #408727) and diluted to a 3 wt. % aqueous solution) was mixed with a 3 wt. % aqueous solution of SR454 multifunctional acrylate (ethoxylated trimethylolpropane triacrylate, Sartomer Corporation, Exton, PA) in a ratio of 4:1 by weight bPEI:SR454 to form the coating formulation. A sample of filter paper (Whatman 410) was dip coated with the coating formulation and then dried at 80° C. for 3 minutes. The dried sample was cut into test strips (20 mm by 40 mm). The coated surface of the test strips was white in color. The test strips were evaluated for color change and color leaching according to the procedure described in Example PI31. The results are reported in Table 10.

TABLE 10

| Test Strip of Example | Test Strip Color after Immersion in 0.1 wt. % OPA | Test Strip Color after Immersion in 0.35 wt. % OPA Bath | Color from Test Strip Leached into 0.35 wt. % OPA Bath |
|---|---|---|---|
| PI31 | pale yellow | yellow | no |
| PI32 | pale yellow | yellow | no |
| PI33 | pale yellow | yellow | no |
| PI34 | not tested | pale yellow | no |
| PI35 | pale yellow | yellow | no |
| PI36 | pale yellow | yellow | no |
| PI37 | pale yellow | yellow | no |
| PI38 | pale yellow | yellow | no |
| PI39 | pale yellow | yellow | no |
| PI40 | pale yellow | yellow | no |
| PI41 | not tested | colorless | no |
| PI42 | pale yellow | yellow | no |

For Examples PI31-PI33 and PI35-PI40 colorimetric analysis of the test strips following immersion in an OPA bath was conducted using an X-Rite SP64 colorimeter (X-Rite Inc.). The collected CIE L*a*b* color scale values (established by the International Commission on Illumination) are reported in Table 11

TABLE 11

| Test Strip of Example | Color Scale for Test Strip after Immersion in 0.1 wt. % OPA | | | Color Scale for Test Strip after Immersion in 0.35 wt. % OPA | | |
|---|---|---|---|---|---|---|
| | L* | a* | b* | L* | a* | b* |
| PI31 | 86.5 | −6.4 | 26.1 | 85.7 | −7.4 | 47.6 |
| PI32 | 87.3 | −3.5 | 13.9 | 85.0 | −7.8 | 48.1 |
| PI33 | 88.4 | −7.1 | 26.8 | 81.2 | −6.6 | 25.9 |
| PI35 | 88.9 | −4.4 | 16.8 | 86.8 | −6.9 | 51.6 |
| PI36 | 89.8 | −3.2 | 13.1 | 86.5 | −7.9 | 51.0 |
| PI37 | 89.5 | −7.1 | 28.7 | 84.0 | −8.3 | 36.5 |
| PI38 | 89.8 | −5.1 | 19.4 | 82.9 | −7.5 | 50.3 |
| PI39 | 87.2 | −3.4 | 13.7 | 86.0 | −8.0 | 52.7 |
| PI40 | 83.2 | −7.2 | 31.3 | 87.3 | −9.1 | 43.3 |

Example PI43

Branched polyethylenimine (MW 25,000 g/mole, available from Sigma-Aldrich Corporation (cat #408727) and diluted to a 3 wt. % aqueous solution) was mixed with a 3 wt. % aqueous solution of 3-(acryloxypropyl)trimethoxysilane (abbreviation of AS) in a ratio of 7:3 by weight bPEI:AS to form Solution I. NEOREZ R966 polyurethane dispersion (abbreviation of "R966", DSM Corporation) was diluted with distilled water to prepare a 3 wt. % solution (Solution J). Solutions I and J were then mixed together in a ratio of 1:9 by weight Solution I: Solution J to form the final coating formulation. A sample of filter paper (Whatman 410) was dip coated with the coating formulation and then dried at 80° C. for 3 minutes. The dried sample was cut into test strips (20 mm by 40 mm). The coated surface of the test strips was white in color.

A testing solution of ortho-phthalaldehyde (OPA) in water was prepared at a concentration of 0.35 wt. % OPA. The test strips were evaluated by immersing a test strip into a bath of the OPA testing solution for 5 minutes with the bath temperature maintained at 25° C. The test strip was removed from the bath and checked for a color change by visual examination. Test strips were evaluated to determine if any indicator color from a test strip leached into the OPA bath using the procedure described in Example PI31. The results are reported in Table 12.

Example PI44

The procedure of Example PI43 was followed, except that Solutions I and J were mixed together in a ratio of 3:7 by weight Solution I:Solution J to form the final coating formulation. The results are reported in Table 12.

Example PI45

The procedure of Example PI43 was followed, except that Solutions I and J were mixed together in a ratio of 1:1 by weight Solution I:Solution J to form the final coating formulation. The results are reported in Table 12.

Example PI46

Branched polyethylenimine (MW 25,000, available from Sigma-Aldrich Corporation (cat #408727) and diluted to a 3 wt. % aqueous solution) was mixed with a 3 wt. % aqueous solution of 3-(acryloxypropyl)trimethoxysilane in a ratio of 1:1 by weight bPEI:AS to form Solution K. R966 polyurethane dispersion was diluted with distilled water to prepare a 3 wt. % solution (Solution L). Solutions K and L were then mixed together in a ratio of 1:9 by weight Solution K:Solution L to form the final coating formulation. A sample of filter paper (Whatman 410) was dip coated with the coating formulation and then dried at 80° C. for 3 minutes. The dried sample was cut into test strips (20 mm by 40 mm). The coated surface of the test strips was white in color. The test strips were evaluated for color change according to the procedure described in Example PI43. Test strips were also evaluated to determine if any indicator color from a test strip leached into the OPA bath using the procedure described in Example PI31. The results are reported in Table 12.

Example PI47

The procedure of Example PI46 was followed, except that Solutions K and L were mixed together in a ratio of 3:7 by weight Solution K: Solution L to form the final coating formulation. The results are reported in Table 12.

Example PI48

The procedure of Example PI46 was followed, except that Solutions K and L were mixed together in a ratio of 1:1 by weight Solution K: Solution L to form the final coating formulation. The results are reported in Table 12, below.

TABLE 12

| Test Strip of Example | Test Strip Color after Immersion in 0.35 wt. % OPA | Color from Test Strip Leached into 0.35 wt. % OPA Bath |
|---|---|---|
| PI43 | pale yellow | no |
| PI44 | yellow | no |
| PI45 | bright yellow | no |
| PI46 | pale yellow | not tested |
| PI47 | yellow | no |
| PI48 | bright yellow | no |

Example PI49

Branched polyethylenimine (MW 25,000 g/mole, available from Sigma-Aldrich Corporation (cat #408727) and diluted to a 2.5 wt. % aqueous solution, abbreviation of "bPEI") was dip coated onto a nylon 6,6 membrane (single reinforced layer nylon three zone membrane with nominal pore size of 1.8 microns, #080ZN, obtained from 3M Purification Inc., Meriden, Conn.) and then dried at 80° C. for 3 minutes. The dried sample was cut into test strips (20 mm by 40 mm). The coated surface of the test strips was white in color.

Individual testing solutions of ortho-phthalaldehyde (OPA) in water were prepared at concentrations of 0.10 wt. %, and 0.35 wt. % OPA. The test strips were evaluated by immersing a test strip into a bath of the OPA testing solution for 5 minutes with the bath temperature maintained at 25° C. The time point at which a color change of the test strip was first observed was recorded. Test strips were also evaluated to determine if any indicator color from a test strip leached into the OPA bath using the procedure described in Example PI31. The results are reported in Table 13.

Example PI50

Branched polyethylenimine (MW 25,000 g/mole, available from Sigma-Aldrich Corporation (cat #408727) and diluted to a 2.5 wt. % aqueous solution) was mixed with a 2.5 wt. % aqueous solution of 3-(acryloxypropyl)trimethoxysilane in a ratio of 9:1 by weight bPEI:AS to form the final coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color. The test strips were evaluated for time to color change according to the procedure described in Example PI49. Test strips were also evaluated to determine if any indicator color from a test strip leached into the OPA bath using the procedure described in Example PI31. The results are reported in Table 13.

Example PI51

The procedure of Example PI50 was followed, except that the ratio of bPEI:AS in the final coating formulation was 4:1. The results are reported in Table 13.

Example PI52

The procedure of Example PI50 was followed, except that the ratio of bPEI:AS in the final coating formulation was 7:3. The results are reported in Table 13.

Example PI53

The procedure of Example PI50 was followed, except that the ratio of bPEI:AS in the final coating formulation was 3:2. The results are reported in Table 13.

Example PI54

The procedure of Example PI50 was followed, except that the ratio of bPEI:AS in the final coating formulation was 1:1. The results are reported in Table 13.

Example PI55

The procedure of Example PI50 was followed, except that the ratio of bPEI:AS in the final coating formulation was 2:3. The results are reported in Table 13, below.

TABLE 13

| Test Strip of Example | bPEI:AS | Time to Color Change after Immersion in 0.1 wt. % OPA (seconds) | Time to Color Change after Immersion in 0.35 wt. % OPA (seconds) | Color from Test Strip Leached into 0.35 wt. % OPA Bath |
|---|---|---|---|---|
| PI49 | 100:0 | 120 | 45 | yes |
| PI50 | 9:1 | 210 | 67 | no |
| PI51 | 4:1 | 260 | 80 | no |
| PI52 | 7:3 | 253 | 115 | no |
| PI53 | 3:2 | no change at 300 | 151 | no |
| PI54 | 1:1 | no change at 300 | 170 | no |
| PI55 | 2:3 | no change at 300 | 183 | no |

Example PI56

Branched polyethylenimine (MW 25,000 g/mole, available from Sigma-Aldrich Corporation (cat #408727) and diluted to a 2.0 wt. % aqueous solution) was dip coated onto a sample of nylon membrane (described in Example PI49) and then dried at 80° C. for 3 minutes. The dried sample was cut into test strips (20 mm by 40 mm). The coated surface of the test strips was white in color. The test strips were evaluated for time to color change according to the procedure described in Example PI49. Test strips were also evaluated to determine if any indicator color from a test strip leached into the OPA bath using the procedure described in Example PI31. The results are reported in Table 14.

Example PI57

Branched polyethylenimine (MW 25,000 g/mole, available from Sigma-Aldrich Corporation (cat #408727) and diluted to a 2.0 wt. % aqueous solution) was mixed with a 2.0 wt. % aqueous solution of 3-(acryloxypropyl)trimethoxysilane (abbreviation of "AS") in a ratio of 9:1 by weight bPEI:AS to form the final coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color. The test strips were evaluated for time to color change according to the procedure described in Example PI49. Test strips were also evaluated to determine if any indicator color from a test strip leached into the OPA bath using the procedure described in Example PI31. The results are reported in Table 14.

Example PI58

The procedure of Example PI57 was followed, except that the ratio of bPEI:AS in the final coating formulation was 4:1. The results are reported in Table 14.

Example PI59

The procedure of Example PI57 was followed, except that the ratio of bPEI:AS in the final coating formulation was 7:3. The results are reported in Table 14.

Example PI60

The procedure of Example PI57 was followed, except that the ratio of bPEI:AS in the final coating formulation was 3:2. The results are reported in Table 14.

Example PI61

The procedure of Example PI57 was followed, except that the ratio of bPEI:AS in the final coating formulation was 1:1. The results are reported in Table 14.

Example PI62

The procedure of Example PI57 was followed, except that the ratio of bPEI:AS in the final coating formulation was 2:3. The results are reported in Table 14, below.

TABLE 14

| Test Strip of Example | bPEI:AS | Time to Color Change after Immersion in 0.1 wt. % OPA, seconds | Time to Color Change after Immersion in 0.35 wt. % OPA, seconds | Color from Test Strip Leached into 0.35 wt. % OPA Bath |
|---|---|---|---|---|
| PI56 | 100:0 | 140 | 50 | yes |
| PI57 | 9:1 | 240 | 75 | no |
| PI58 | 4:1 | 260 | 87 | no |
| PI59 | 7:3 | no change at 300 | 120 | no |
| PI60 | 3:2 | no change at 300 | 160 | no |

TABLE 14-continued

| Test Strip of Example | bPEI:AS | Time to Color Change after Immersion in 0.1 wt. % OPA, seconds | Time to Color Change after Immersion in 0.35 wt. % OPA, seconds | Color from Test Strip Leached into 0.35 wt. % OPA Bath |
|---|---|---|---|---|
| PI61 | 1:1 | no change at 300 | 180 | no |
| PI62 | 2:3 | no change at 300 | 210 | no |

Example PI63

Branched polyethylenimine (MW 25,000 g/mole, available from Sigma-Aldrich Corporation (cat #408727) and diluted to a 2.5 wt. % aqueous solution) was mixed with a 2.5 wt. % aqueous solution of SR454 multifunctional acrylate in a ratio of 4:1 by weight bPEI:SR454 to form the coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color. The test strips were evaluated for the time to color change according to the procedure described in Example PI49. Test strips were also evaluated to determine if any indicator color from a test strip leached into the OPA bath using the procedure described in Example PI31. The results are reported in Table 15.

Example PI64

The procedure of Example PI63 was followed, except that the ratio of bPEI: SR454 in the final coating formulation was 7:3. The results are reported in Table 15.

Example PI65

The procedure of Example PI63 was followed, except that the ratio of bPEI:SR454 in the final coating formulation was 3:2. The results are reported in Table 15.

Example PI66

The procedure of Example PI63 was followed, except that the ratio of bPEI:SR454 in the final coating formulation was 1:1. The results are reported in Table 15.

Example PI67

The procedure of Example PI63 was followed, except that the ratio of bPEI:SR454 in the final coating formulation was 2:3. The results are reported in Table 15, below.

TABLE 15

| Test Strip of Example | bPEI:SR454 | Time to Color Change after Immersion in 0.1 wt. % OPA, seconds | Time to Color Change after Immersion in 0.35 wt. % OPA, seconds | Color from Test Strip Leached into 0.35 wt. % OPA Bath |
|---|---|---|---|---|
| PI63 | 4:1 | 180 | 40 | no |
| PI64 | 7:3 | 210 | 63 | no |
| PI65 | 3:2 | 260 | 86 | no |
| PI66 | 1:1 | no change at 300 | 97 | no |
| PI67 | 2:3 | no change at 300 | 145 | no |

Example PI68

Branched polyethylenimine (MW 800, available from Sigma-Aldrich Corporation (cat #408719), abbreviation of "bPEI800") and diluted to a 2.5 wt. % aqueous solution) was mixed with a 2.5 wt. % aqueous solution of SR454 multifunctional acrylate in ratios of either 7:3, 1:1, or 2:3 by weight bPEI800:SR454 to form three separate coating formulations. Separate samples of nylon membrane (described in Example PI49) were dip coated with one of the formulations and then dried at 80° C. for 3 minutes. The dried samples were cut into test strips (20 mm by 40 mm). The coated surface of the test strips was white in color. When the test strips were immersed into OPA baths according to the procedure described in Example PI31 leaching of color into the test bath was observed for all of the test strips (visual examination). The greatest amount of color leaching was observed for the sample prepared with 9:1 ratio of bPEI800:SR454. The least amount of color leaching was observed for the sample with a 2:3 ratio of bPEI800:SR454.

Example PI69

Branched polyethylenimine (MW 25,000 g/mole, available from Sigma-Aldrich Corporation (cat #408727) and diluted to a 2.5 wt. % aqueous solution, abbreviation of "bPEI") was mixed with a 2.5 wt. % aqueous solution of SR454 multifunctional acrylate in a ratio of 9:1 by weight bPEI: SR454 to form the coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color.

A testing solution of ortho-phthalaldehyde (OPA) in water was prepared at a concentration of 0.35 wt. % OPA. The test strips were evaluated by immersing a test strip into a bath of the OPA testing solution for 5 minutes with the bath temperature maintained at 25° C. The test strip was removed from the bath and checked for a color change from white to yellow. Test strips were also evaluated to determine if any indicator color from a test strip leached into the OPA bath using the procedure described in Example PI31. The results are reported in Table 16.

Example PI70

Branched polyethylenimine (MW 25,000 g/mole, available from Sigma-Aldrich Corporation (cat #408727) and diluted to a 2.5 wt. % aqueous solution, abbreviation of "bPEI") was mixed with a 2.5 wt. % aqueous solution of SR454 multifunctional acrylate in a ratio of 9:1 by weight bPEI: SR454 to form Solution M. NEOCRYL A612 was diluted with distilled water to prepare a 2.5 wt. % solution (Solution N). Solutions M and N were then mixed together in a ratio of 1:1 by weight Solution M:Solution N to form the final coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color. The test strips were evaluated by immersion in an OPA bath according to the procedure described in Example PI69. The results are reported in Table 16.

Example PI71

Branched polyethylenimine (MW 25,000 g/mole, available from Sigma-Aldrich Corporation (cat #408727) and diluted to a 2.5 wt. % aqueous solution, abbreviation of "bPEI") was mixed with a 2.5 wt. % aqueous solution of SR454 multifunctional acrylate in a ratio of 9:1 by weight bPEI: SR454 to form Solution M. NEOREZ R966 polyurethane dispersion was diluted with distilled water to prepare a 2.5 wt. % solution (Solution O). Solutions M and O were then mixed together in a ratio of 1:1 by weight Solution M:Solution O to form the final coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color. The test strips were evaluated by immersion in an OPA bath according to the procedure described in Example PI69. The results are reported in Table 16.

Example PI72

The procedure of Example PI69 was followed, except that the ratio of bPEI:SR454 in the final coating formulation was 7:3. The results are reported in Table 16.

Example PI73

Branched polyethylenimine (MW 25,000 g/mole, available from Sigma-Aldrich Corporation (cat #408727) and diluted to a 2.5 wt. % aqueous solution, abbreviation of "bPEI") was mixed with a 2.5 wt. % aqueous solution of SR454 multifunctional acrylate in a ratio of 7:3 by weight bPEI: SR454 to form Solution P. NEOCRYL A612 was diluted with distilled water to prepare a 2.5 wt. % solution (Solution Q). Solutions P and Q were then mixed together in a ratio of 1:1 by weight Solution P:Solution Q to form the final coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color. The test strips were evaluated by immersion in an OPA bath according to the procedure described in Example PI69. The results are reported in Table 16.

Example PI74

Branched polyethylenimine (MW 25,000 g/mole, available from Sigma-Aldrich Corporation (cat #408727) and diluted to a 3 wt. % aqueous solution, abbreviation of "bPEI") was mixed with a 2.5 wt. % aqueous solution of SR454 multifunctional acrylate in a ratio of 7:3 by weight bPEI:SR454 to form Solution P. NEOREZ R966 polyurethane dispersion was diluted with distilled water to prepare a 2.5 wt. % solution (Solution R). Solutions P and R were then mixed together in a ratio of 1:1 by weight Solution P:Solution R to form the final coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color. The test strips were evaluated by immersion in an OPA bath according to the procedure described in Example PI69. The results are reported in Table 16, below.

TABLE 16

| Test Strip of Example | Color of Test Strip after 5 min Immersion in 0.35 wt. % OPA | Color from Test Strip Leached into 0.35 wt. % OPA Bath |
|---|---|---|
| PI69 | yellow | yes |
| PI70 | yellow | yes |
| PI71 | yellow | yes |
| PI72 | bright yellow | no |
| PI73 | bright yellow | no |
| PI74 | bright yellow | no |

Example PI75

Branched polyethylenimine (MW 25,000 g/mole, available from Sigma-Aldrich Corporation (cat #408727) and diluted to a 2.5 wt. % aqueous solution) was mixed with a 2.5 wt. % aqueous solution of crosslinker 3-glycidoxypropyl trimethoxysilane (abbreviation="GPS", available from Gelest Inc.) in ratios of either 9:1, 4:1, or 7:3 by weight bPEI:crosslinker to form three separate coating formulations. Separate samples of nylon membrane (described in Example PI49) were dip coated with one of the formulations and then dried at 80° C. for 3 minutes. The dried samples were cut into test strips (20 mm by 40 mm). The coated surface of the test strips was white in color. The test strips were immersed into OPA baths according to the procedure described in Example PI49. The test strips were evaluated for time to color change according to the procedure described in Example PI49. Test strips were also evaluated to determine if any indicator color from a test strip leached into the OPA bath using the procedure described in Example PI31. The results are reported in Table 17. In addition, in a separate experiment the color of each strip was determined by visual inspection after being immersed in the OPA bath for 80 seconds and 300 seconds. At the 80 second time point, the test strips were a very pale yellow color. At the 300 second time point the test strips were a bright yellow color.

TABLE 17

| Test Strip of Example | bPEI:crosslinker | Time to Color Change after Immersion in 0.1 wt. % OPA (seconds) | Time to Color Change after Immersion in 0.35 wt. % OPA (seconds) | Color from Test Strip Leached into 0.35 wt. % OPA Bath |
|---|---|---|---|---|
| PI75 | 9:1 | 210 | 67 | no |
| PI75 | 4:1 | 260 | 80 | no |
| PI75 | 7:3 | 293 | 115 | no |

Example PI76

Branched polyethylenimine (MW 25,000 g/mole, available from Sigma-Aldrich Corporation (cat #408727) and diluted to a 2.5 wt. % aqueous solution, abbreviation of "bPEI") was mixed with a 2.5 wt. % aqueous solution of 3-(acryloxypropyl)trimethoxysilane (abbreviation of "AS") in a ratio of 4:1 by weight bPEI:AS to form the final coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color.

Individual testing solutions of ortho-phthalaldehyde (OPA) in water were prepared at concentrations of 0.10 wt. %, and 0.35 wt. % OPA. The test strips were evaluated by immersing a test strip into a bath prepared from the testing solution and maintained at either 10° C., 20° C., 25° C., or 30° C.

The test strips were also immersed in the bath for varying periods of time (1.0, 1.35, 1.62, or 5 minutes). Prior to immersion in the OPA bath some of the test strips were immersed in a bath of 1% Intercept detergent (Medivators Inc.) for 7.5 minutes followed by immersion in a fresh distilled water bath for an additional 7.5 minutes and then air drying. Each test sample was removed from the OPA bath and the reflectance measurement of the test strip was determined at an emitted wavelength 450 nm using an X-Rite Handheld Spectrophotometer X-Rite eXact NGH Handheld Spectrophotometer with a 1.5 mm aperture (X-Rite Inc.). The mean reflectance values (n=3) and corresponding test conditions are reported in Table 18, below.

TABLE 18

| OPA Conc. In Bath, wt. % | Bath Temp, ° C. | Immersion Time, minutes | Pretreatment with Detergent | Reflectance, % |
|---|---|---|---|---|
| 0.35 | 30 | 1.0 | yes | 41 |
| 0.35 | 25 | 1.35 | yes | 47 |
| 0.35 | 20 | 1.62 | yes | 57 |
| 0.35 | 10 | 5 | yes | 55 |
| 0.35 | 25 | 5 | yes | 30 |
| 0.35 | 30 | 1.0 | no | 50 |
| 0.35 | 25 | 1.35 | no | 47 |
| 0.35 | 20 | 1.62 | no | 63 |
| 0.35 | 10 | 5 | no | 68 |
| 0.35 | 25 | 5 | no | 27 |
| 0.10 | 25 | 5 | yes | 50 |
| 0.10 | 25 | 5 | no | 55 |

Example PI77

Branched polyethylenimine (MW 25,000 g/mole, available from Sigma-Aldrich Corporation (cat #408727) and diluted to a 2.5 wt. % aqueous solution, abbreviation of "bPEI") was mixed with a 2.5 wt. % aqueous solution of NEOREZ R966 polyurethane dispersion in a weight ratio of 1:1 to form the coating formulation. A sample of nylon membrane (described in Example PI49) was coated with a #24 Meyer rod and then dried at 80° C. for 3 minutes. The dried sample was cut into test strips (20 mm by 40 mm). The coated surface of the test strips was white in color.

A testing solution of ortho-phthalaldehyde (OPA) in water was prepared at a concentration of 0.35 wt. % OPA. The test strips were evaluated by immersing a test strip into a bath of the OPA testing solution for either 1.35 or 5 minutes with the bath temperature maintained at 25° C. Each test sample was removed from the bath and the reflectance measurement of the test strip was determined at an emitted wavelength 440 nm using an X-Rite Handheld Spectrophotometer X-Rite eXact NGH Handheld Spectrophotometer with a 1.5 mm aperture (X-Rite Inc.). The mean reflectance values (n=3) and corresponding test conditions are reported in Table 19.

Example PI78

Branched polyethylenimine (MW 25,000 g/mole, available from Sigma-Aldrich Corporation (cat #408727) and diluted to a 2.5 wt. % aqueous solution, abbreviation of "bPEI") was mixed with a 2.5 wt. % aqueous solution of 3-(acryloxypropyl)trimethoxysilane (abbreviation of "AS") in a weight ratio of 7:3 to form the coating formulation. A sample of nylon membrane (described in Example PI49) was coated with a #24 Meyer rod and then dried at 80° C. for 3 minutes. The dried sample was cut into test strips (20 mm by 40 mm). The coated surface of the test strips was white in color. The test strips were evaluated by immersion in an OPA bath according to the procedure described in Example PI77. The mean reflectance values (n=3) and corresponding test conditions are reported in Table 19.

Example PI79

Branched polyethylenimine (MW 25,000 g/mole, available from Sigma-Aldrich Corporation (cat #408727) and diluted to a 2.5 wt. % aqueous solution, abbreviation of "bPEI") was mixed with a 2.5 wt. % aqueous solution of 3-(acryloxypropyl)trimethoxysilane (abbreviation of "AS") in a weight ratio of 7:3 to form Solution S. NEOREZ R966 polyurethane dispersion was diluted with distilled water to prepare a 2.5 wt. % solution (Solution T). Solutions S and T were then mixed together to form a final coating formulation with a weight ratio of 7:3:7 bPEI:AS:R966. A sample of nylon membrane (described in Example PI49) was coated with a #24 Meyer rod and then dried at 80° C. for 3 minutes. The dried sample was cut into test strips (20 mm by 40 mm). The coated surface of the test strips was white in color. The test strips were evaluated by immersion in an OPA bath according to the procedure described in Example PI77. The mean reflectance values (n=3) and corresponding test conditions are reported in Table 19, below.

TABLE 19

| Test Strip of Example | Immersion Time, min | wt. % OPA | Reflectance, % |
|---|---|---|---|
| PI77 | 1.35 | 0.35 | 73 |
| PI77 | 5 | 0.35 | 55 |
| PI78 | 1.35 | 0.35 | 67 |
| PI78 | 5 | 0.35 | 18 |
| PI79 | 1.35 | 0.35 | 70 |
| PI79 | 5 | 0.35 | 14 |

Example PI80

Branched polyethylenimine (abbreviation of bPEI, MW 60,000 g/mole as a 50 wt. % solution in water) was mixed with a 30 wt. % polyurethane dispersion (#CS 8057, Incorez Copolymer Ltd., United Kingdom) and distilled water to form a coating formulation with a ratio of 1:3 by weight bPEI:polyurethane dispersion. The coating formulation (50 microliters) was applied as a circular dot to the surface of an injection molded chip (60 mm by 50 mm by 1 mm) of BAYBLEND T85 stock white (a polycarbonate (PC) and acrylonitrile butadiene styrene (ABS) blend; available from Bayer Material Science, Leverkusen, Germany). The chip with coated test dot was then dried at 100° C. for 15 minutes resulting in a clear coating over the white substrate.

Individual testing solutions of ortho-phthalaldehyde (OPA) in water were prepared at concentrations of 0.35 wt. %, and 0.575 wt. % OPA. The coated chips were evaluated by immersing the coated portion of the chip into a bath prepared from the testing solution and maintained at 25° C. The chips were immersed in the bath for either 1.35 minutes or 5 minutes. Each chip was removed from the bath and the coated dot was checked by visual inspection for a change in color from white to yellow. The results are reported in Table 20.

Example PI81

The procedure of Example PI80 was followed, except that the ratio of bPEI:polyurethane dispersion in the coating formulation was set at 1:1 by weight.

Example PI82

The procedure of Example PI79 was followed, except that the ratio of bPEI:polyurethane dispersion in the coating formulation was set at 3:1 by weight.

TABLE 20

| | | Color of Test Dot following Immersion in Bath | | |
|---|---|---|---|---|
| Example | bPEI:polyurethane dispersion | 1.35 min in 0.35 wt. % OPA | 5 min in 0.35 wt. % OPA | 5 min in 0.575 wt. % OPA |
| PI80 | 1:3 | very pale yellow | pale yellow | pale yellow |
| PI81 | 1:1 | very pale yellow | yellow | yellow |
| PI82 | 3:1 | very pale yellow | bright yellow | bright yellow |

Example PI83

A testing solution of ortho-phthalaldehyde (OPA) in water was prepared at a concentration of 0.35 wt. % OPA. Test chips prepared according to Example PI79 were evaluated by immersing the coated portion of a test chip into a bath prepared from a testing solution with the bath temperature maintained at either 20° C., 25° C., or 30° C. The test chips were immersed in the bath for varying periods of time (1.0, 1.35, 1.62, or 5 minutes). Each test chip was removed from the bath and reflectance of the test dot was determined at an emitted wavelength of 440 nm using an X-Rite Handheld Spectrophotometer X-Rite eXact NGH Handheld Spectrophotometer with a 1.5 mm aperture (X-Rite Inc.). The mean reflectance values (n=3) and the corresponding test conditions are reported in Table 21.

Example PI84

The same testing procedure as reported in Example PI83 was followed, except that prior to immersion in the OPA bath the coated chips were immersed in a bath of 1% Intercept detergent (Medivators, Inc.) for 7.5 minutes followed by immersion in a fresh distilled water bath for an additional 7.5 minutes and then air drying.

TABLE 21

| Example | Bath Temp (° C.) | Immersion Time (minutes) | Detergent Used in method | Reflectance (%) |
|---|---|---|---|---|
| PI84 | 30 | 1.0 | yes | 28 |
| PI84 | 25 | 1.35 | yes | 20 |
| PI84 | 20 | 1.62 | yes | 24 |
| PI84 | 25 | 5 | yes | 5 |
| PI83 | 30 | 1.0 | no | 35 |
| PI83 | 25 | 1.35 | no | 23 |
| PI83 | 20 | 1.62 | no | 27 |
| PI83 | 25 | 5 | no | 13 |

Examples PI85-PI93

The coating formulations for Examples PI85-PI93 were prepared by pre-mixing branched polyethylenimine (bPEI, MW 60,000 g/mole as a 50 wt. % solution in water, available from Thermo Fisher Scientific, that was diluted to 10 wt. % in water) and R966 (10 wt. % in water). The crosslinkers 3-glycidoxypropyl trimethoxysilane (abbreviation="GPS" and prepared as 10 wt. % in isopropyl alcohol) and PZ-28 (a polyfunctional aziridine available from PolyAziridine LLC., Medford, N.J.) and prepared as 10 wt. % in isopropyl alcohol) were added next with continued mixing to provide the specified coating formulations. The amount of each component (as 10 wt. % solutions) in a formulation is listed in Table 22. Each coating formulation was individually coated onto a separate clear PET polyester film substrate (5 mil) using a #24 Meyer rod. The coated films were dried at 85° C. for 5-10 minutes to form a clear coat. Test strips (about 25 mm by 102 mm) were prepared from the coated films. A bath of OPA (0.575 wt. % in water) was prepared and each test strip was evaluated by immersing the test strip in the bath for 300 seconds. The bath was maintained at 25° C. The color of the test strip was determined by visual inspection after being immersed for 80 seconds and 300 seconds. The integrity of the test strip was determined by visually inspecting each test strip at 300 seconds for any signs of haze, cracking, blister formation, or swelling. In addition, test strips were evaluated to determine if any indicator color from a test strip leached into the OPA bath. For this test a new test strip was immersed and maintained in a fresh OPA bath (0.575 wt. % at 25° C.) for 30 minutes. The bath contained the minimum amount of OPA to fully cover the test strip (typically 1-2 mL). The test strip was then removed from the bath and the bath liquid was checked for color change by visual examination (no leaching=colorless bath, while leaching=change in bath color from colorless to either a pale yellow or yellow color). The results for color change (at 80 and 300 seconds), test strip integrity, and leaching are reported in Table 23.

TABLE 22

| Example | bPEI, g | R966, g | GPS, g | PZ-28, g |
|---------|---------|---------|--------|----------|
| PI85 | 5 | 5 | 0 | 0.15 |
| PI86 | 5 | 5 | 0 | 0.3 |
| PI87 | 5 | 5 | 0 | 0.45 |
| PI88 | 4 | 6 | 0 | 0.3 |
| PI89 | 3 | 7 | 0 | 0.15 |
| PI90 | 5 | 5 | 0.25 | 0.45 |
| PI91 | 6 | 4 | 0.6 | 0.2 |
| PI92 | 7 | 3 | 0.7 | 0.15 |
| PI93 | 8 | 2 | 0.8 | 0.1 |

TABLE 23

| Example | Color after Immersion for 80 sec | Color after Immersion for 300 sec | Test Strip Integrity | Color from Test Strip Leached into 0.575 wt. % OPA Bath |
|---------|----------------------------------|-----------------------------------|----------------------|----------------------------------------------------------|
| PI85 | clear to very pale yellow | bright yellow | no issue | yes |
| PI86 | clear to very pale yellow | bright yellow | no issue | yes |
| PI87 | clear to very pale yellow | bright yellow | no issue | yes |
| PI88 | pale yellow | bright yellow | no issue | no |
| PI89 | pale yellow | bright yellow | no issue | no |
| PI90 | pale yellow | bright yellow | no issue | no |
| PI91 | clear to very pale yellow | bright yellow | no issue | no |
| PI92 | clear to very pale yellow | bright yellow | no issue | no |
| PI93 | pale yellow | bright yellow | no issue | no |

Examples PI94-PI100

The coating formulations for Examples PI94-PI100 were prepared by pre-mixing branched polyethylenimine (bPEI, MW 60,000 g/mole as a 50 wt. % solution in water, available from Thermo Fisher Scientific, that was diluted to 10 wt. % in water) and R966 (10 wt. % in water). The crosslinker GPS (neat liquid) or AS (neat liquid) was added next with continued mixing to form the specified coating formulations. The amount of each component in a formulation is listed in Table 24. Each coating formulation was individually coated onto a separate clear PET polyester film substrate (5 mil) using a #24 Meyer rod. The coated films were dried at 85° C. for 5-10 minutes to form a clear coat. Test strips (about 25 mm by 102 mm) were prepared from the coated films.

The test strips were evaluated for color change (at 80 and 300 seconds) and for integrity of the test strip according to the procedure described for Example PI85. The results are reported in Table 25.

TABLE 24

| Example | bPEI, g | R966, g | GPS, g | AS, g |
|---------|---------|---------|--------|-------|
| PI94 | 60 | 40 | 0 | 0.6 |
| PI95 | 60 | 40 | 0.6 | 0 |
| PI96 | 70 | 30 | 0 | 0.7 |
| PI97 | 80 | 20 | 0 | 0.8 |
| PI98 | 80 | 20 | 0.8 | 0 |
| PI99 | 90 | 10 | 0 | 0.9 |
| PI100 | 95 | 5 | 0 | 0.95 |

TABLE 25

| Example | Color after Immersion for 80 sec | Color after Immersion for 300 sec | Test Strip Integrity |
|---------|----------------------------------|-----------------------------------|----------------------|
| PI94 | clear to very pale yellow | bright yellow | no issue |
| PI95 | clear to very pale yellow | bright yellow | no issue |
| PI96 | clear to very pale yellow | bright yellow | no issue |
| PI97 | clear to very pale yellow | bright yellow | no issue |
| PI98 | clear to very pale yellow | bright yellow | slight cracking |
| PI99 | not determined | not determined | cracking |
| PI100 | not determined | not determined | cracking |

Example PI101

Branched polyethylenimine (bPEI, MW 60,000 g/mole as a 50 wt. % solution in water, available from Thermo Fisher Scientific, that was diluted to 10 wt. % in water), crosslinker AS (neat liquid), and polyvinyl alcohol (POVAL 49-88, available from Kuraray Ltd., Singapore; abbreviation="PVA") were mixed together to form the coating formulation (amounts listed in Table 26). The coating formulation was coated onto a clear PET polyester film substrate (5 mil) using a #24 Meyer rod and then dried at 85° C. for 5-10 minutes to form a clear coat. Test strips (about 25 mm by 102 mm) were prepared from the coated film.

The test strips were evaluated for color change (at 80 and 300 seconds) and for integrity of the test strip according to the procedure described for Example PI85. The results are reported in Table 27.

Example PI102

Branched polyethylenimine (bPEI, MW 60,000 g/mole as a 50 wt. % solution in water, available from Thermo Fisher Scientific, that was diluted to 10 wt. % in water), crosslinker AS (neat liquid), and polyvinyl pyrrolidone (K90, MW=360,000 g/mole, available from Sigma-Aldrich Corporation, abbreviation=PVP) were mixed together to form the coating formulation (amounts listed in Table 26). The coating formulation was coated onto a clear PET polyester film substrate (5 mil) using a #24 Meyer rod and then dried at 85° C. for 5-10 minutes to form a clear coat. Test strips (about 25 mm by 102 mm) were prepared from the coated film.

The test strips were evaluated for color change (at 80 and 300 seconds) and for integrity of the test strip according to the procedure described for Example PI85. The results are reported in Table 27.

Examples PI103-PI107

The coating formulations for Examples PI103-PI107 were prepared by pre-mixing branched polyethylenimine (bPEI, MW 60,000 g/mole as a 50 wt. % solution in water, available from Thermo Fisher Scientific that was diluted to 10 wt. % in water) and R966 (10 wt. % in water). With continued mixing the crosslinker AS (neat liquid) was added followed by the addition of PVA (10 wt. % solution in water). The amount of each component in a formulation is listed in Table 26. Each coating formulation was individually coated onto a separate clear PET polyester film substrate (5 mil) using a #24 Meyer rod. The coated films were dried at 85° C. for 5-10 minutes to form a clear coat. Test strips (about 25 mm by 102 mm) were prepared from the coated films.

The test strips were evaluated for color change (at 80 and 300 seconds) and for integrity of the test strip according to the procedure described for Example PI85. The results are reported in Table 27.

TABLE 26

| Example | bPEI, g | R966, g | AS, g | PVA, g | PVP, g |
| --- | --- | --- | --- | --- | --- |
| PI101 | 50 | 0 | 0.5 | 50 | 0 |
| PI102 | 50 | 0 | 0.5 | 0 | 50 |
| PI103 | 50 | 25 | 0.5 | 25 | 0 |
| P1104 | 50 | 16.7 | 0.5 | 33.3 | 0 |
| P1105 | 50 | 12.5 | 0.5 | 37.5 | 0 |
| PI106 | 70 | 15 | 0.7 | 15 | 0 |
| PI107 | 30 | 35 | 0.3 | 35 | 0 |

TABLE 27

| Example | Color after Immersion for 80 sec | Color after Immersion for 300 sec | Test Strip Integrity |
| --- | --- | --- | --- |
| PI101 | clear to very pale yellow | bright yellow | slight cracking and haze |
| PI102 | not determined | not determined | slight cracking and haze |

TABLE 27-continued

| Example | Color after Immersion for 80 sec | Color after Immersion for 300 sec | Test Strip Integrity |
| --- | --- | --- | --- |
| PI103 | clear to very pale yellow | bright yellow | haze |
| PI104 | clear to very pale yellow | bright yellow | slight haze |
| PI105 | clear to very pale yellow | bright yellow | haze |
| PI106 | pale yellow | bright yellow | slight haze |
| PI107 | clear to very pale yellow | bright yellow | haze |

Examples PI108-PI119

The coating formulations for Examples PI108-PI119 were prepared by pre-mixing branched polyethylenimine (bPEI, MW 60,000 g/mole as a 50 wt. % solution in water, available from Thermo Fisher Scientific, that was diluted to 10 wt. % in water) and R966 (10 wt. % in water). The crosslinkers 3-(acryloxypropyl)trimethoxysilane (abbreviation ="AS", and prepared as 10 wt. % in isopropyl alcohol) and PZ-28 (prepared as 10 wt. % in isopropyl alcohol) were added next with continued mixing to form the specified coating formulations. The amount of each component (as 10 wt. % solutions) in a formulation is listed in Table 28. Each coating formulation was individually coated onto a separate clear PET polyester film substrate (5 mil) using a #24 Meyer rod. The coated films were dried at 85° C. for 5-10 minutes to form a clear coat. Test strips (about 25 mm by 102 mm) were prepared from the coated films. The test strips were evaluated for color change (at 80 and 300 seconds), color leaching, and test strip integrity according to the procedure described for Example PI85. The results are reported in Table 29.

TABLE 28

| Example | bPEI, g | R966, g | AS, g | PZ-28, g |
| --- | --- | --- | --- | --- |
| PI108 | 7 | 3 | 0.7 | 0 |
| PI109 | 7 | 3 | 0.7 | 0.15 |
| PI110 | 7 | 3 | 0.35 | 0 |
| PI111 | 7 | 3 | 0.35 | 0.15 |
| PI112 | 5 | 5 | 0.5 | 0 |
| PI113 | 5 | 5 | 0.5 | 0.25 |
| PI114 | 5 | 5 | 0.25 | 0.25 |
| PI115 | 5 | 5 | 0.7 | 0.15 |
| PI116 | 3 | 7 | 0.3 | 0 |
| PI117 | 3 | 7 | 0.3 | 0.35 |
| PI118 | 3 | 7 | 0.15 | 0 |
| PI119 | 3 | 7 | 0.15 | 0.35 |

TABLE 29

| Example | Color after Immersion for 80 sec | Color after Immersion for 300 sec | Test Strip Integrity | Color from Test Strip Leached into 0.575 wt. % OPA Bath |
| --- | --- | --- | --- | --- |
| PI108 | clear to very pale yellow | bright yellow | no issue | no |
| PI109 | clear to very pale yellow | bright yellow | no issue | no |
| PI110 | clear to very pale yellow | bright yellow | no issue | yes |
| PI111 | clear to very pale yellow | bright yellow | no issue | no |
| PI112 | clear to very pale yellow | bright yellow | no issue | no |
| PI113 | clear to very pale yellow | bright yellow | no issue | no |
| PI114 | clear to very pale yellow | bright yellow | no issue | no |
| PI115 | clear to very pale yellow | bright yellow | no issue | no |
| PI116 | pale yellow | bright yellow | no issue | no |
| PI117 | pale yellow | bright yellow | no issue | no |
| PI118 | pale yellow | bright yellow | no issue | no |
| PI119 | pale yellow | bright yellow | no issue | no |

Examples PI120-PI124

The coating formulations for Examples PI120-PI124 were prepared by pre-mixing branched polyethylenimine (bPEI, MW 60,000 g/mole as a 50 wt. % solution in water, available from Thermo Fisher Scientific, that was diluted to 10 wt. % in water) and R966 (10 wt. % in water). The crosslinkers 3-(acryloxypropyl)trimethoxysilane (abbreviation="AS", and prepared as 10 wt. % in isopropyl alcohol) and PZ-28 (prepared as 10 wt. % in isopropyl alcohol) were added next with continued mixing to form the specified coating formulations. The amount of each component in a formulation (as 10 wt. % solutions) is listed in Table 30. Each coating formulation was individually coated onto a separate clear PET polyester film substrate (10 mil) using a #30 Meyer rod. The coated films were dried at 110° C. for 10 minutes to form a clear coat. Test strips (about 25 mm by 102 mm) were prepared from the coated films. A testing solution of orthophthalaldehyde (OPA) in water was prepared at a concentration of 0.35 wt. % OPA. The test strips were evaluated by immersing a test strip into a bath of the OPA testing solution for either 1.35 or 5 minutes with the bath temperature maintained at 25° C. Following immersion the test strip was removed from the testing solution, immersed in a fresh bath of distilled water for 15 minutes, and then rinsed with isopropyl alcohol for about 5 seconds. The test strip was placed on a white background and the reflectance measurement of the test strip was determined at an emitted wavelength 450 nm using an X-Rite Handheld Spectrophotometer X-Rite eXact NGH Handheld Spectrophotometer with a 4 mm aperture (X-Rite Inc.). The mean reflectance values (n=3) and corresponding test conditions are reported in Table 31.

TABLE 30

| Example | bPEI, g | R966, g | AS, g | PZ-28, g |
| --- | --- | --- | --- | --- |
| PI120 | 5 | 5 | 0.25 | 0 |
| PI121 | 3 | 7 | 0.15 | 0 |
| PI122 | 7 | 3 | 0.7 | 0 |
| PI123 | 7 | 3 | 0.7 | 0.15 |
| PI124 | 5 | 5 | 0.5 | 0.25 |

TABLE 31

| | Mean Reflectance, % | |
| --- | --- | --- |
| Test Strip of Example | OPA Bath Immersion Time of 1.35 Min | OPA Bath Immersion Time of 5 Min |
| PI120 | 49 | 15 |
| PI121 | 58 | 34 |
| PI122 | 43 | 8 |
| PI123 | 51 | 12 |
| PI124 | 58 | 16 |

Examples PI125-PI127

The coating formulations for Examples PI125-PI127 were prepared by pre-mixing branched polyethylenimine (bPEI, MW 60,000 g/mole as a 50 wt. % solution in water, available from Thermo Fisher Scientific, that was diluted to 10 wt. % in water) and polyacrylic dispersion A612 (10 wt. % in water). The crosslinkers 3-glycidoxypropyl trimethoxysilane (GPS, neat) and PZ-28 (prepared as 10 wt. % in isopropyl alcohol) were added next with continued mixing to form the specified coating formulations. The amount of each component in a formulation is listed in Table 32. Each coating formulation was individually coated onto a separate clear PET polyester film substrate (5 mil) using a #24 Meyer rod. The coated films were dried at 85° C. for 5-10 minutes to form a clear coat. Test strips (about 25 mm by 102 mm) were prepared from the coated films. The test strips were evaluated for color change (at 80 and 300 seconds), color leaching, and test strip integrity according to the procedure described for Example PI85. The results are reported in Table 33.

TABLE 32

| Example | bPEI (10 wt. %), g | A612 (10 wt. %), g | GPS (neat), g | PZ-28 (10 wt. %), g |
| --- | --- | --- | --- | --- |
| PI125 | 7 | 3 | 0.07 | 0.15 |
| PI126 | 5 | 5 | 0.05 | 0.25 |
| PI127 | 3 | 7 | 0.03 | 0.35 |

TABLE 33

| Example | Color after Immersion for 80 sec | Color after Immersion for 300 sec | Test Strip Integrity | Color from Test Strip Leached into 0.575 wt. % OPA Bath |
| --- | --- | --- | --- | --- |
| PI125 | pale yellow | bright yellow | no issue | no |
| PI126 | pale yellow | bright yellow | no issue | no |
| PI127 | pale yellow | bright yellow | no issue | no |

Examples PI128-PI129

Branched polyethylenimine (bPEI, MW 60,000 g/mole as a 50 wt. % solution in water, available from Thermo Fisher Scientific that was diluted to 5 wt. % in water) and diethyl glutaconate (Sigma-Aldrich Corporation) were mixed together to form the coating formulations (amounts listed in Table 34). Separate samples of nylon membrane (described in Example PI49) were dip coated with one of the coating formulations. The coated samples were dried at 120° C. for 5 minutes to form a clear coat. Test strips (about 25 mm by 102 mm) were prepared from the coated samples.

The test strips were evaluated for color change (at 80 and 300 seconds) and for leaching according to the procedure described for Example PI85. In addition, the time point at which a color change of the test strip was first observed was recorded. The results are reported in Table 35.

TABLE 34

| Example | bPEI (5 wt. %), g | Diethyl glutaconate (neat), g |
| --- | --- | --- |
| PI128 | 9 | 0.05 |
| PI129 | 5 | 0.25 |

TABLE 35

| Example | Time to Initial Color Change (seconds) | Color after Immersion for 80 sec | Color after Immersion for 300 sec | Color from Test Strip Leached into 0.575 wt. % OPA Bath |
|---|---|---|---|---|
| PI128 | 43 | clear to very pale yellow | brown-yellow | no |
| PI129 | 47 | clear to very pale yellow | brown-yellow | no |

Examples PI130-PI132

The coating formulations for Examples PI130-PI132 were prepared by mixing ethoxylated polyethylenimine (MW 50,000 g/mole as a 37 wt. % solution in water, available from Sigma-Aldrich Corporation that was diluted to 5 wt. % in water) and 3-(acryloxypropyl)trimethoxysilane (abbreviation of "AS", Gelest Inc.) in the amounts listed in Table 36. Separate samples of nylon membrane (described in Example PI49) were dip coated with one of the coating formulations. The coated samples were dried at 120° C. for 5 minutes to form a clear coat. Test strips (about 25 mm by 102 mm) were prepared from the coated samples.

The test strips were evaluated for color change (at 80 and 300 seconds) and for leaching according to the procedure described for Example PI85. In addition, the time point at which a color change of the test strip was first observed was recorded. The results are reported in Table 37.

TABLE 36

| Example | Ethoxylated polyethylenimine (5 wt. %), g | AS (neat), g |
|---|---|---|
| PI130 | 10 | 0 |
| PI131 | 10 | 0.1 |
| PI132 | 10 | 0.2 |

TABLE 37

| Example | Time to Initial Color Change (seconds) | Color after Immersion for 80 sec | Color after Immersion for 300 sec | Color from Test Strip Leached into 0.575 wt. % OPA Bath |
|---|---|---|---|---|
| PI130 | 17 | pale yellow | bright yellow | yes |
| PI131 | 56 | pale yellow | bright yellow | no |
| PI132 | 67 | very pale yellow | bright yellow | no |

Example PI133

The coating formulation was prepared by first mixing 7 g of branched polyethylenimine (bPEI, MW 60,000 g/mole as a 50 wt. % solution in water, available from Thermo Fisher Scientific, that was diluted to 10 wt. % in water) and 3 g of R966 (10 wt. % in water). The crosslinkers diethyl glutaconate (0.14 g, neat) and PZ-28 (0.15 g, prepared as 10 wt. % in isopropyl alcohol) were added next with continued mixing to form the coating formulation. The formulation was coated onto a clear PET polyester film substrate (10 mil) using a #24 Meyer rod. The coated film was dried at 120° C. for 5 minutes to form a clear coat. Test strips (about 25 mm by 102 mm) were prepared from the coated films. Test strips were evaluated for color change (at 80 and 300 seconds), color leaching, and test strip integrity according to the procedure described for Example PI85. The results are reported in Table 38, below.

TABLE 38

| Example | Color after Immersion for 80 sec | Color after Immersion for 300 sec | Test Strip Integrity | Color from Test Strip Leached into 0.575 wt. % OPA Bath |
|---|---|---|---|---|
| PI133 | clear to very pale yellow | bright yellow | no issue | no |

Example PI134

The coating formulation was prepared by first mixing 6.3 g of branched polyethylenimine (bPEI, MW 60,000 g/mole as a 50 wt. % solution in water, available from Thermo Fisher Scientific, that was diluted to 10 wt. % in water) and 2.7 g of R966 (10 wt. % in water). The crosslinkers 3-(acryloxypropyl)trimethoxysilane (0.63 g of a 10 wt. % solution in isopropyl alcohol) and PZ-28 (0.14 g of a 10 wt. % in isopropyl alcohol) were added next with continued mixing. Finally, 1 g of Nalco 1115, aqueous silica nanoparticle dispersion (spherical, 4 nm, 15 wt. %; available from Nalco Company, Naperville, Ill.) was added with mixing to form the coating formulation. The formulation was coated onto a clear PET polyester film substrate (10 mil) using a #24 Meyer rod. The coated film was dried at 120° C. for 5 minutes to form a clear coat. Test strips (about 25 mm by 102 mm) were prepared from the coated films. The test strips were evaluated for color change (at 80 and 300 seconds), color leaching, and test strip integrity according to the procedure described for Example PI85. The results are reported in Table 39.

Example PI135

A modified silica nanoparticle dispersion was prepared by adding with mixing 1.77 g of 3-aminopropyltriethoxysilane (Sigma-Aldrich Corporation) was added with mixing to 50 g of a 10 wt. % Nalco 1115 aqueous silica nanoparticle dispersion. The resulting dispersion was heated at 80° C. for 12 hours and then cooled to room temperature.

The coating formulation was prepared by first mixing 6.3 g of branched polyethylenimine (bPEI, MW 60,000 g/mole as a 50 wt. % solution in water, available from Thermo Fisher Scientific, that was diluted to 10 wt. % in water) and 2.7 g of R966 (10 wt. % in water). The crosslinkers 3-(acryloxypropyl)trimethoxysilane (0.63 g of a 10 wt. % solution in isopropyl alcohol) and PZ-28 (0.14 g of a 10 wt. % in isopropyl alcohol) were added next with continued mixing. Finally, 1 g the modified silica nanoparticle dispersion (described above) was added with mixing to form the coating formulation. The formulation was coated onto a clear PET polyester film substrate (10 mil) using a #24 Meyer rod. The coated film was dried at 120° C. for 5 minutes to form a clear coat. Test strips (about 25 mm by 102 mm) were prepared from the coated films. The test strips were evaluated for color change (at 80 and 300 seconds), color leaching, and test strip integrity according to the procedure described for Example PI85. The results are reported in Table 39, below.

TABLE 39

| Example | Color after Immersion for 80 sec | Color after Immersion for 300 sec | Test Strip Integrity | Color from Test Strip Leached into 0.575 wt. % OPA Bath |
|---|---|---|---|---|
| PI134 | pale yellow | bright yellow | no issue | no |
| PI135 | clear to very pale yellow | bright yellow | no issue | no |

Examples PI136-PI139

The coating formulations for Examples PI136-PI139 were prepared by pre-mixing branched polyethylenimine (bPEI, MW 60,000 g/mole as a 50 wt. % solution in water, available from Thermo Fisher Scientific, that was diluted to 5 wt. % with added ethanol) with a 5 wt. % ethanol solution of SR415 multifunctional acrylate (20 mole ethoxylated trimethylolpropane triacrylate, Sartomer Corporation). Next the photoinitiator IRGACURE 184 (1-hydroxy-cyclohexyl phenyl ketone, BASF Corporation, Florham Park, N.J.) was added with mixing followed by optional addition of a 5 wt. % solution of R966 in ethanol with continued mixing. The amount of each component in a formulation is listed in Table 40. Each of the resulting coating formulations was individually coated onto a separate clear PET polyester film substrate (5 mil) using a #24 Meyer rod. The coated films were dried at 100° C. for 5 minutes and then cured under a nitrogen atmosphere by 3 passes through a UV curing station (model MC-6RQN, Fusion UV Curing Inc., Rockville, Md.) with a Fusion H-type lamp at a speed of 12.2 meters/minute to form a clear coating. Test strips (about 25 mm by 102 mm) were prepared from the coated films. The test strips were evaluated for color change (at 80 and 300 seconds), color leaching, and test strip integrity according to the procedure described for Example PI85. The results are reported in Table 41.

TABLE 40

| Example | bPEI (5 wt. %), g | SR415 (5 wt. %), g | R966 (5 wt. %), g | IRGACURE 184, mg |
|---|---|---|---|---|
| PI136 | 9 | 1 | 0 | 10 |
| PI137 | 7 | 3 | 0 | 30 |
| PI138 | 8.5 | 1.5 | 4.3 | 15 |
| PI139 | 3 | 3 | 4.4 | 30 |

TABLE 41

| Example | Color after Immersion for 80 sec | Color after Immersion for 300 sec | Test Strip Integrity | Color from Test Strip Leached into 0.575 wt. % OPA Bath |
|---|---|---|---|---|
| PI136 | clear to very pale yellow | bright yellow | no issue | no |
| PI137 | clear to very pale yellow | bright yellow | no issue | no |
| PI138 | clear to very pale yellow | bright yellow | no issue | no |
| PI139 | clear to very pale yellow | bright yellow | no issue | no |

Example PI140

Nalco 1115, an aqueous silica nanoparticle dispersion (spherical, 4 nm, 15 wt. %; available from Nalco Company), was diluted to 5 wt. % with added distilled water and then adjusted to a pH of 2-3 by the addition of concentrated nitric acid. The resulting pH adjusted dispersion was coated onto a paper substrate using a #6 Meyer rod. The coated paper was dried at 120° C. for 5 minutes. The dried sample was cut into test strips (10 mm by 100 mm) and the test strips were dip coated with a coating solution that was prepared by adding 0.5 mL of water to 70 g of a 10 wt. % solution of 3-aminopropyltrimethoxysilane (Sigma-Aldrich Corporation) in ethyl alcohol. The dip coated test strips were dried at 80° C. for 5 minutes.

Testing solutions of ortho-phthalaldehyde (OPA) in water were prepared at concentrations of 0.35 wt. %, and 0.575 wt. % OPA. Test strips were evaluated by first immersing a test strip in a vortexing water bath for 30 seconds and then immediately immersing in a testing solution bath according to one of the following evaluation Protocols J-O. For Protocol-J a test strip was immersed for 100 seconds in the 0.35 wt. % OPA bath with the bath temperature maintained at 25° C. For Protocol-K a test strip was immersed for 4 minutes in the 0.35 wt. % OPA bath with the bath temperature maintained at 20° C.

For Protocol-K a test strip was immersed for 5 minutes in the 0.35 wt. % OPA bath with the bath temperature maintained at 25° C. For Protocol-K a test strip was immersed for 100 seconds in the 0.575 wt. % OPA bath with the bath temperature maintained at 25° C. For Protocol-N a test strip was immersed for 5 minutes in the 0.575 wt. % OPA bath with the bath temperature maintained at 25° C. For Protocol-O a test strip was immersed for 12 minutes in the 0.575 wt. % OPA bath with the bath temperature maintained at 20° C. For each of the Protocols J-O, following immersion for the designated period of time, the test sample was removed from the testing solution, immersed in a fresh bath of distilled water for 15 minutes, and then rinsed with isopropyl alcohol for about 5 seconds. The rinsed samples were air dried. The reflectance measurement of each test strip was determined at an emitted wavelength of 510 nm using an X-Rite Handheld Spectrophotometer X-Rite eXact NGH Handheld Spectrophotometer with a 1.5 mm aperture (X-Rite Inc.). The mean reflectance values (n=4) for Protocols J-O are reported in Table 42, below.

TABLE 42

| | Bath Temperature, ° C. | Immersion Time | wt. % OPA | Reflectance, % |
|---|---|---|---|---|
| Protocol-J | 25 | 100 sec | 0.35 | 80 |
| Protocol-K | 20 | 4 min | 0.35 | 78 |
| Protocol-L | 25 | 5 min | 0.35 | 75 |
| Protocol-M | 25 | 100 sec | 0.575 | 77 |
| Protocol-N | 25 | 5 min | 0.575 | 78 |
| Protocol-O | 20 | 12 min | 0.575 | 73 |

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A method of disinfecting a medical device, the method comprising:
    a) contacting a disinfectant with a process indicator and the medical device,
    wherein the medical device is a lumened device comprising at least one internal conduit;
    wherein a process indicator module comprises the process indicator;
    wherein the disinfectant is circulated through the process indicator module and the at least one internal conduit; and
    wherein the disinfectant comprises at least one aldehyde, wherein the process indicator comprises a layer comprising a crosslinked branched polyethylenimine is e-bean grafted on a substrate, wherein the crosslinked branched polyethylenimine is reactive with the disinfectant to form at least one adduct, wherein the crosslinked branched polyethylenimine and the medical device are in fluid communication through the disinfectant, wherein a predetermined disinfectant exposure criterion exists for contacting the disinfectant with the medical device, and wherein the crosslinked branched polyethylenimine comprises at least one of primary amino groups or secondary amino groups; and
    b) spectrally observing the process indicator and obtaining at least one parameter therefrom that is predictive of the predetermined disinfectant exposure criterion; and
    c) determining that the predetermined disinfectant exposure criterion has been achieved.

2. The method of claim 1, wherein the crosslinked branched polyethylenimine comprises a crosslinked silylated branched polyethylenimine.

3. The method of claim 1, wherein the crosslinked branched polyethylenimine is chemically bonded to silica.

4. The method of claim 1, wherein the disinfectant comprises at least one dialdehyde.

5. The method of claim 1, wherein the disinfectant comprises at least one of glutaraldehyde or ortho-phthalaldehyde.

6. The method of claim 1, wherein the crosslinked branched polyethylenimine is admixed with an inert polymeric binder.

7. The method of claim 1, wherein the predetermined disinfectant exposure criterion corresponds to an industry recognized standard for disinfection of the medical device.

8. The method of claim 1, wherein the lumened device comprises an endoscope.

9. The method of claim 1, wherein the at least one parameter comprises optical reflectance.

10. The method of claim 1, wherein the at least one parameter comprises a visible color.

11. The method of claim 1, wherein the at least one process parameter indicator is continuously obtained.

12. The method of claim 1, wherein the process indicator module is in parallel flow with the at least one internal conduit.

13. The method of claim 1, wherein the process indicator module is in linear flow with the at least one internal conduit.

14. A method of disinfecting a lumened medical device with at least one internal conduit, the method comprising:
    a) contacting a disinfectant comprising at least one aldehyde with the medical device and a process indicator module comprising a process indicator such that the disinfectant is circulated through the process indicator module and the at least one internal conduit in the medical device; and
    wherein the process indicator comprises an indicator layer disposed on a substrate, the indicator layer comprising a crosslinked branched polyethylenimine comprises silylated polyethylenimine reactive with the disinfectant to form at least one adduct, wherein the indicator layer and the medical device are in fluid communication through the disinfectant, and wherein a predetermined disinfectant exposure criterion exists for contacting the disinfectant with the medical device;
  b) spectrally observing the indicator layer of the process indicator and obtaining at least one parameter therefrom that is predictive of the predetermined disinfectant exposure criterion; and
  c) determining that the predetermined disinfectant exposure criterion has been achieved.

15. The method of claim 14, wherein the crosslinked branched polyethylenimine is e-beam grafted to the substrate.

16. The method of claim 14, wherein the crosslinked branched polyethylenimine is reacted with a guanylating agent to provide a guanidino-functional compound.

17. A method of disinfecting a lumened medical device with at least one internal conduit, the method comprising:
  a) contacting a disinfectant comprising at least one aldehyde with the medical device and a process indicator module comprising a process indicator such that the disinfectant is circulated through the process indicator module and the at least one internal conduit in the medical device; and
  wherein the process indicator comprises an indicator layer disposed on a substrate, the indicator layer comprising a crosslinked branched guanylated polyethylenimine reactive with the disinfectant to form at least one adduct, wherein the indicator layer and the medical device are in fluid communication through the disinfectant, and wherein a predetermined disinfectant exposure criterion exists for contacting the disinfectant with the medical device;
  b) spectrally observing the indicator layer of the process indicator and obtaining at least one parameter therefrom that is predictive of the predetermined disinfectant exposure criterion; and
  c) determining that the predetermined disinfectant exposure criterion has been achieved.

18. The method of claim 17, wherein the crosslinked branched guanylated polyethylenimine is e-beam grafted to the substrate.

19. The method of claim 17, wherein the crosslinked branched guanylated polyethylenimine is chemically bonded to silica.

20. The method of claim 17, wherein the disinfectant comprises at least one dialdehyde.

21. The method of claim 17, wherein the disinfectant comprises at least one of glutaraldehyde or ortho-phthalaldehyde.

* * * * *

UNITED STATES PATENT AND TRADEMARK OFFICE
CERTIFICATE OF CORRECTION

PATENT NO. : 10,792,383 B2
APPLICATION NO. : 16/096776
DATED : October 6, 2020
INVENTOR(S) : Naiyong Jing It is certified that error appears in the above-identified patent and that said Letters Patent is hereby corrected as shown below:

In the Specification

Column 1
Line 8                    Delete "PCT/US2017/029370 ," and insert -- PCT/US2017/029370, --, therefor.

Column 3
Line 57                   Delete "colonscope," and insert -- colonoscope, --, therefor.

Column 4
Line 25                   Delete "Appin." and insert -- Appln. --, therefor.
Line 56                   Delete "thereof" and insert -- thereof. --, therefor.

Column 8
Line 11                   Delete "(e.g," and insert -- (e.g., --, therefor.

Column 13
Lines 7-8                 Delete "3-isocyanatopropyltriethoxyilane" and insert -- 3-isocyanatopropyltriethoxysilane --, therefor.

Column 18
Line 27                   Delete "color" and insert -- color. --, therefor.

Column 28
Line 67                   Delete "11" and insert -- 11. --, therefor.

Column 36
Lines 3-19 (Approx.)      Delete "aqueous solution of SR454 multifunctional acrylate in a ratio of 7:3 by weight bPEI:SR454 to form Solution P. NEOREZ R966 polyurethane dispersion was diluted with distilled water to prepare a 2.5 wt. % solution Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,792,383 B2

|  |  |
|---|---|
|  | (Solution R). Solutions P and R were then mixed together in a ratio of 1:1 by weight Solution P:Solution R to form the final coating formulation. A sample of nylon membrane (described in Example PI49) was dip coated with the coating formulation and then dried at 80° C. for 3 minutes. The dried sample was cut into test strips (20 mm by 40 mm). The coated surface of the test strips was white in color. The test strips were evaluated by immersion in an OPA bath according to the procedure described in Example PI69. The results are reported in Table 16, below." and insert the same on Column 36, Line 2, as a continuation of the same paragraph. |
| Column 44 Lines 27-34 (Approx.) | Delete "PET polyester film substrate (5 mil) using a #24 Meyer rod. The coated films were dried at 85° C. for 5-10 minutes to form a clear coat. Test strips (about 25 mm by 102 mm) were prepared from the coated films. The test strips were evaluated for color change (at 80 and 300 seconds), color leaching, and test strip integrity according to the procedure described for Example PI85. The results are reported in Table 29." and insert the same on Column 44, Line 26, as a continuation of the same paragraph. |
| Column 47 Lines 18-25 | Delete "Corporation that was diluted to 5 wt. % in water) and 3-(acryloxypropyl)trimethoxysilane (abbreviation of "AS", Gelest Inc.) in the amounts listed in Table 36. Separate samples of nylon membrane (described in Example PI49) were dip coated with one of the coating formulations. The coated samples were dried at 120° C. for 5 minutes to form a clear coat. Test strips (about 25 mm by 102 mm) were prepared from the coated samples." and insert the same on Column 47, Line 17, as a continuation of the same paragraph. |